(12) United States Patent
Miyake et al.

(10) Patent No.: US 11,101,442 B2
(45) Date of Patent: Aug. 24, 2021

(54) ORGANIC ELECTROLUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventors: Hideo Miyake, Yokohama (JP); Takuya Uno, Yokohama (JP); Ichinori Takada, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 346 days.

(21) Appl. No.: 16/038,981

(22) Filed: Jul. 18, 2018

(65) Prior Publication Data

US 2019/0189950 A1    Jun. 20, 2019

(30) Foreign Application Priority Data

Dec. 19, 2017   (KR) .................. 10-2017-0174912

(51) Int. Cl.
  *H01L 51/50* (2006.01)
  *H01L 51/52* (2006.01)
  (Continued)

(52) U.S. Cl.
  CPC ........ *H01L 51/5024* (2013.01); *C07D 333/76* (2013.01); *C07D 409/14* (2013.01);
  (Continued)

(58) Field of Classification Search
  None
  See application file for complete search history.

(56) References Cited

U.S. PATENT DOCUMENTS

| 8,632,716 B2 | 1/2014 | Fukushima |
| 9,590,186 B2 | 3/2017 | Itoi et al. |
| 2018/0331290 A1* | 11/2018 | Miyake ................. H01L 51/006 |

FOREIGN PATENT DOCUMENTS

| CN | 106467542 A | * | 3/2017 | ............. C09K 11/06 |
| CN | 106467542 A | * | 3/2017 | ............. H01L 51/50 |

(Continued)

OTHER PUBLICATIONS

EPO Extended Search Report dated Jul. 4, 2019, for corresponding European Patent Application No. 18211757.2 (8 pages).

*Primary Examiner* — Gregory D Clark
(74) *Attorney, Agent, or Firm* — Lewis Roca Rothgerber Christie LLP

(57) ABSTRACT

An organic electroluminescence device and an amine compound for an organic electroluminescence device are provided. The amine compound according to an embodiment of the present disclosure is represented by Formula 1. In Formula 1, Ar is a substituted or unsubstituted aryl group having 10 to 60 carbon atoms for forming a ring:

Formula 1

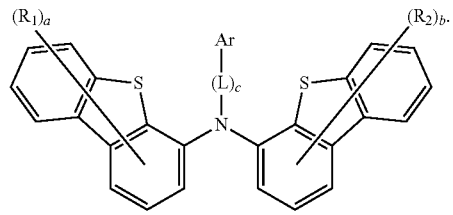

23 Claims, 1 Drawing Sheet

(51) Int. Cl.
*H01L 51/00* (2006.01)
*C07D 409/14* (2006.01)
*C07D 333/76* (2006.01)
*C09K 11/06* (2006.01)

(52) U.S. Cl.
CPC .......... *C09K 11/06* (2013.01); *H01L 51/0052* (2013.01); *H01L 51/0058* (2013.01); *H01L 51/0061* (2013.01); *H01L 51/0074* (2013.01); *H01L 51/5092* (2013.01); *H01L 51/5096* (2013.01); *H01L 51/5218* (2013.01); *H01L 51/5234* (2013.01); *H01L 51/0081* (2013.01); *H01L 51/5056* (2013.01); *H01L 51/5072* (2013.01)

(56) References Cited

FOREIGN PATENT DOCUMENTS

| CN | 2017-1090119 | * | 9/2017 |
|---|---|---|---|
| EP | 2502908 A1 | | 9/2012 |
| EP | 3078721 A1 | | 10/2016 |
| EP | 3401313 A1 | | 11/2018 |
| JP | 2016-108292 A | | 6/2016 |
| KR | 10-2016-0059609 | | 5/2016 |
| KR | 10-1623879 | | 5/2016 |
| KR | 10-2016-0113783 | | 10/2016 |
| KR | 10-2016-0143627 | | 12/2016 |
| KR | 10-1751473 | | 6/2017 |
| KR | 10-1825542 | | 2/2018 |
| WO | WO 2011/148909 A1 | | 12/2011 |
| WO | WO 2013/109027 A1 | | 7/2013 |
| WO | WO 2018/216903 A1 | | 11/2018 |

* cited by examiner

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

This application claims priority to and the benefit of Korean Patent Application No. 10-2017-0174912, filed on Dec. 19, 2017, the entire content of which is hereby incorporated by reference.

BACKGROUND

The present disclosure herein relates to an organic electroluminescence device and an amine compound for an organic electroluminescence device.

The development of an organic electroluminescence display device as an image display device is being actively conducted. The organic electroluminescence display device is different from a liquid crystal display device. The organic electroluminescence display device is a self-luminescent display device in which holes and electrons injected from a first electrode and a second electrode, respectively, recombine in an emission layer, and a light emission material including an organic compound in the emission layer emits light to realize the display of images.

As an organic electroluminescence device, an organic device including, for example, a first electrode, a hole transport layer disposed (e.g., positioned) on the first electrode, an emission layer disposed on the hole transport layer, an electron transport layer disposed on the emission layer, and a second electrode disposed on the electron transport layer is known. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light generated by the transition of the excitons to a ground state. However, an embodiment of the configuration of the organic electroluminescence device is not limited thereto, but various modifications may be possible. In the application of an organic electroluminescence device to a display apparatus, the increase of efficiency and life of the organic electroluminescence device is required (or desired).

SUMMARY

One or more aspects of embodiments of the present disclosure are directed toward an organic electroluminescence device having high emission efficiency and long life.

One or more aspects of embodiments of the present disclosure are directed toward an amine compound applicable to an organic electroluminescence device having high emission efficiency and long life.

An embodiment of the present disclosure provides an organic electroluminescence device including a first electrode, a hole transport region disposed on the first electrode, an emission layer disposed on the hole transport region, an electron transport region disposed on the emission layer, and a second electrode disposed on the electron transport region.

The hole transport region includes an amine compound represented by the following Formula 1:

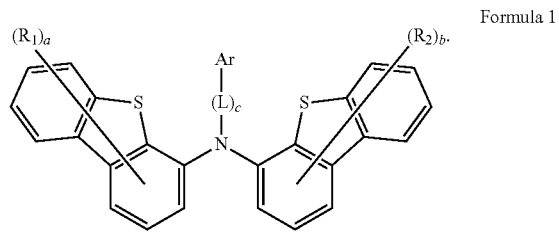

Formula 1

In Formula 1, Ar is a substituted or unsubstituted aryl group having 10 to 60 carbon atoms for forming a ring; L is a substituted or unsubstituted arylene group having 6 to 30 carbon atoms for forming a ring; $R_1$ and $R_2$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; "a" and "b" are each independently an integer of 0 to 7; and "c" is an integer of 1 to 4.

In an embodiment, the hole transport region may include a hole injection layer disposed on the first electrode, and a hole transport layer disposed on the hole injection layer. The hole transport layer may include the amine compound represented by Formula 1.

In an embodiment, the hole transport region may include a plurality of layers. A layer making contact with the emission layer, among the plurality of layers, may include the amine compound represented by Formula 1.

In an embodiment, L may be a substituted or unsubstituted phenylene group, or a substituted or unsubstituted naphthylene group In an embodiment, the amine compound represented by Formula 1 may be represented by one of the following Formulae 2-1 to 2-3:

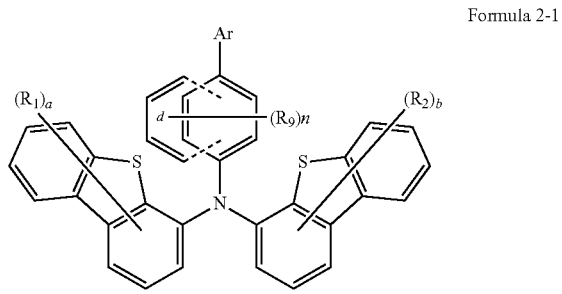

Formula 2-1

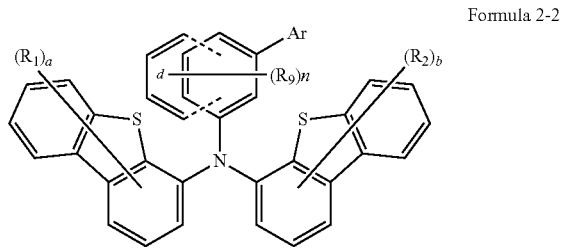

Formula 2-2

Formula 2-3

Formula 2-2-2

In Formulae 2-1 to 2-3, "d" is 0 or 1; $R_9$ is hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; "n" is an integer of 0 to 6; and Ar, $R_1$, $R_2$, "a" and "b" are the same as defined above.

In an embodiment, the amine compound represented by one of Formulae 2-1 to 2-3 may be represented by one of the following Formulae 2-1-1 to 2-3-2:

Formula 2-1-1

Formula 2-3-1

Formula 2-3-2

Formula 2-1-2

In Formulae 2-1-1 to 2-3-2, n1, n3 and n5 are each independently an integer of 0 to 4, n2, n4 and n6 are each independently an integer of 0 to 6, and Ar, $R_1$, $R_2$, $R_9$, "a" and "b" are the same as defined above.

In an embodiment, Ar may be a substituted or unsubstituted naphthyl group, or a substituted or unsubstituted phenanthryl group.

In an embodiment, the amine compound represented by Formula 1 may be represented by one of the following Formulae 3-1 to 3-3:

Formula 2-2-1

Formula 3-1

-continued

Formula 3-2

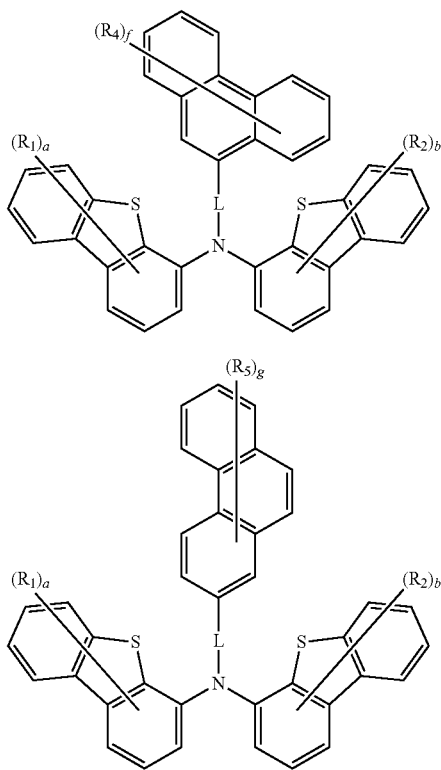

Formula 3-3

In Formulae 3-1 to 3-3, $R_3$ to $R_5$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; "e" is an integer of 0 to 7, and "f" and "g" are each independently an integer of 0 to 9.

In Formulae 3-1 to 3-3, $R_1$, $R_2$, "a", "b", and L are the same as defined above.

In an embodiment, at least one of "a" or "b" may be 1 or 2; and $R_1$ and $R_2$ may be each independently deuterium, a halogen atom, a substituted or unsubstituted alkyl group having 1 to 10 carbon atoms, a substituted or unsubstituted phenyl group, a substituted or unsubstituted naphthyl group, a substituted or unsubstituted phenanthryl group, a substituted or unsubstituted carbazolyl group, a substituted or unsubstituted dibenzofuranyl group, or a substituted or unsubstituted dibenzothiophenyl group.

In an embodiment, the amine compound represented by Formula 1 may be represented by the following Formula 4:

Formula 4

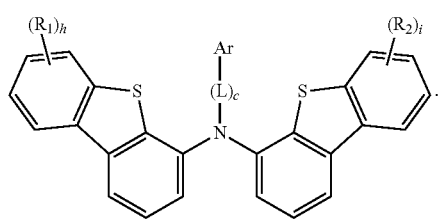

In Formula 4, "h" and "i" are each independently an integer of 0 to 2, at least one of "h" or "i" is 1 or 2, $R_1$ and $R_2$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring.

In Formula 4, Ar, L and "c" are the same as defined above.

In an embodiment, the amine compound represented by Formula 1 may be represented by the following Formula 5:

Formula 5

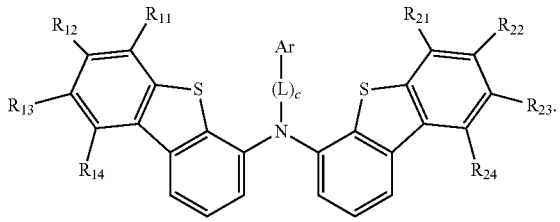

In Formula 5, $R_{11}$ to $R_{14}$ and $R_{21}$ to $R_{24}$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, where at least one of $R_{11}$ to $R_{14}$ and $R_{21}$ to $R_{24}$ is deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. Two members in at least one group selected from $R_{11}$ and $R_{21}$, $R_{12}$ and $R_{22}$, $R_{13}$ and $R_{23}$, and $R_{14}$ and $R_{24}$ are different from each other.

In Formula 5, Ar, L and "c" are the same as defined above.

In an embodiment of the present disclosure, an amine compound represented by Formula 1 is provided.

In an embodiment of the present disclosure, an amine compound represented by Formula 6 is provided:

Formula 6

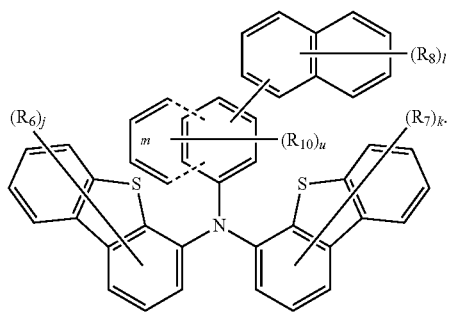

In Formula 6, $R_6$, $R_7$ and $R_{10}$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; each $R_8$ is independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, where a plurality of $R_8$ groups may be connected to form a ring; "j" and "k" are each independently an integer of 0 to 7, "l" is an integer of 0 to 7, "m" is an integer of 0 or 1, and "u" is an integer of 0 to 6.

BRIEF DESCRIPTION OF THE FIGURES

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
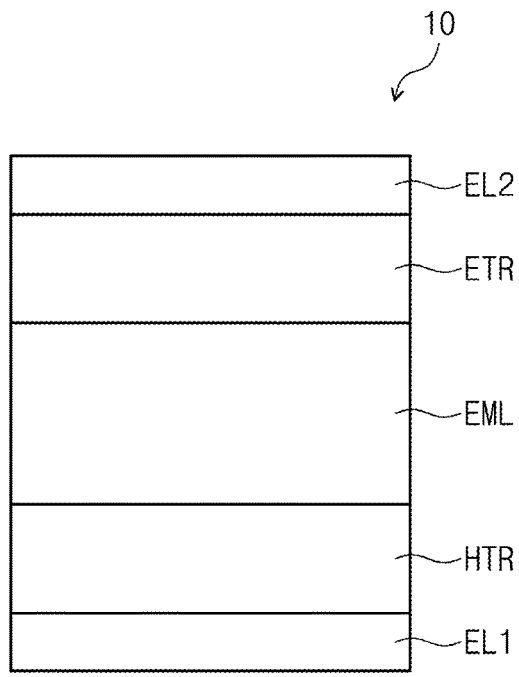
FIG. 1 is a cross-sectional view schematically illustrating an organic electroluminescence device according to an embodiment of the present disclosure.

The above objects, other objects, features and advantages of the present disclosure will be easily understood from the description of example embodiments with reference to the accompanying drawings. The present disclosure may, however, be embodied in different forms and should not be construed as limited to the embodiments set forth herein. Rather, example embodiments are provided so that the contents disclosed herein are thorough and complete, and the spirit of the present disclosure is sufficiently accepted (e.g., apparent) for a person skilled in the art.

Like reference numerals refer to like elements for explaining each drawing. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening parts (e.g., layers) may also be present. When a layer, a film, a region, a plate, etc. is referred to as being "under" another part, it can be "directly under" the other part, or intervening parts (e.g., layers) may also be present.

First, an organic electroluminescence device according to an embodiment of the present disclosure will be explained referring to FIG. 1 and FIG. 2.

FIG. 1 is a cross-sectional view schematically illustrating an organic electroluminescence device according to an embodiment of the present disclosure. FIG. 2 is a cross-sectional view schematically illustrating an organic electroluminescence device according to an embodiment of the present disclosure.

Figure 2:
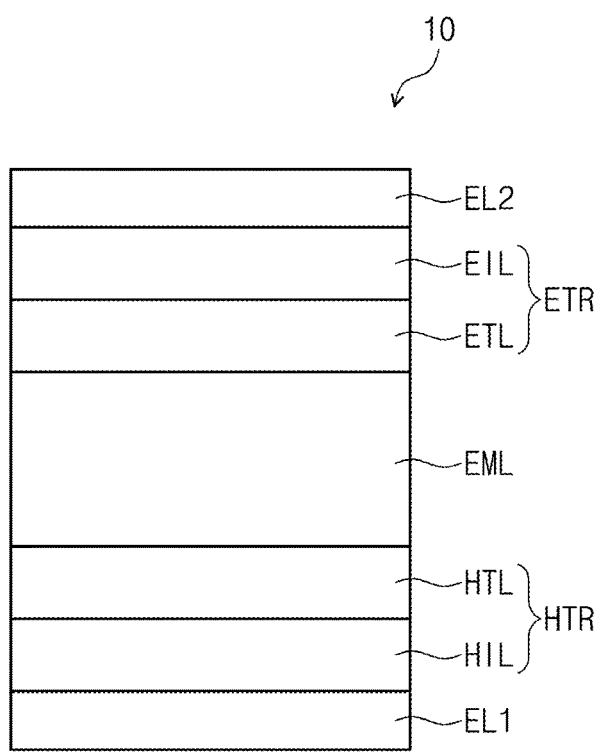
FIG. 2 is a cross-sectional view schematically illustrating an organic electroluminescence device according to an embodiment of the present disclosure.

Referring to FIG. 1 and FIG. 2, an organic electroluminescence device according to an embodiment of the present disclosure includes a first electrode EL1, a hole transport region HTR, an emission layer EML, an electron transport region ETR and a second electrode EL2.

The hole transport region HTR includes an amine compound according to an embodiment of the present disclosure. Hereinafter, the amine compound according to an embodiment of the present disclosure will be explained in more detail and then, each layer of an organic electroluminescence device 10 will be explained.

The amine compound according to an embodiment of the present disclosure is represented by the following Formula 1:

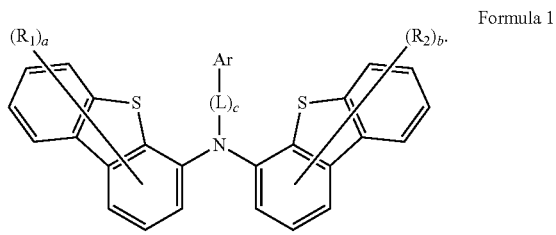

Formula 1

In Formula 1, L may be a substituted or unsubstituted arylene group having 6 to 30 carbon atoms for forming a ring. For example, L may be a substituted or unsubstituted phenylene group, or a substituted or unsubstituted naphthylene group.

Ar may be a substituted or unsubstituted aryl group having 10 to 60 carbon atoms for forming a ring. For example, Ar may be a substituted or unsubstituted naphthyl group, or a substituted or unsubstituted phenanthryl group.

$R_1$ and $R_2$ may each independently be hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. $R_1$ and $R_2$ may be each independently deuterium, a halogen atom, a substituted or unsubstituted alkyl group having 1 to 10 carbon atoms, a substituted or unsubstituted phenyl group, a substituted or unsubstituted naphthyl group, a substituted or unsubstituted phenanthryl group, a substituted or unsubstituted carbazolyl group, a substituted or unsubstituted dibenzofuranyl group, or a substituted or unsubstituted dibenzothiophenyl group. For example, both $R_1$ and $R_2$ may be hydrogen atoms.

"a" and "b" may be each independently an integer of 0 to 7. For example, "a" and "b" may be each independently an integer of 0 to 2. If "a" is 1, $R_1$ may not be hydrogen, and if "b" is 1, $R_2$ may not be hydrogen. If "a" is 0, the amine compound represented by Formula 1 may not be substituted with $R_1$. If "b" is 0, the amine compound represented by Formula 1 may not be substituted with $R_2$. For example, both "a" and "b" may be 0, and a dibenzothiophene group in the amine compound represented by Formula 1 may be unsubstituted. If "a" is an integer of 2 or more, a plurality of $R_1$ groups may be the same or different. If "b" is an integer of 2 or more, a plurality of $R_2$ groups may be the same or different.

"c" is an integer of 1 to 4. If "c" is an integer of 2 or more, a plurality of L groups may be the same or different. If "c" is an integer of 2 or more, L groups may be connected in a line. For example, if L is plural (e.g., if Formula 1 has more than one L group), one L group may be connected with N, another L group may be connected with Ar, and the remaining L groups may be connected between L which is connected with N and L which is connected with Ar. For example, "c" may be 2, and a plurality of L groups may be respectively a phenylene group and a naphthylene group, and the phenylene group and the naphthylene group may be connected in a line. In some embodiments, "c" may be 1, and N and Ar may be connected via one phenylene or naphthylene group.

In the present description,

may refer to a part to be connected (e.g., a binding site).

In the present description, "substituted or unsubstituted" may refer to a group that is unsubstituted or that is substituted with at least one substituent selected from deuterium, a halogen group, a cyano group, a nitro group, an amino group, a silyl group, an oxy group, a thio group, a sulfinyl group, a sulfonyl group, a carbonyl group, a boron group, an aryl amine group, a phosphine oxide group, a phosphine sulfide group, an alkyl group, an alkenyl group, an aryl group, and a heterocycle. In addition, each of the substituent groups listed above may itself be substituted or unsubstituted. For example, a biphenyl group may be described as an aryl group, or as a phenyl group substituted with a phenyl group.

In the present description, the terms "forming a ring via the combination with an adjacent group" may refer to forming a substituted or unsubstituted hydrocarbon ring, or a substituted or unsubstituted heterocycle via the combination of one group with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may each independently be monocyclic or polycyclic. In addition, the ring formed via the combination with an adjacent group may be combined with another ring to form a Spiro structure.

In the present description, the terms "an adjacent group" may refer to a pair of substituent groups where the first substituent is connected to an atom which is directly connected to another atom substituted with the second substituent, a pair of substituent groups connected to the same atom, or a pair of substituent groups where the first substituent is sterically positioned at the nearest position to the second substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the present description, the direct linkage may refer to a single bond.

In the present description, the halogen atom may include a fluorine atom, a chlorine atom, a bromine atom and/or an iodine atom, but is not limited thereto.

In the description, the alkyl group may be a linear, branched or cyclic group.

The carbon number of the alkyl group may be from 1 to 30, from 1 to 20, 1 to 15, from 1 to 10, or from 1 to 6. The alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present description, the aryl group may refer to a functional group or substituent derived from an aromatic hydrocarbon ring. The aryl group may be a monocyclic aryl group or a polycyclic aryl group. The carbon number for forming a ring in the aryl group may be, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without limitation.

In the present description, the fluorenyl group may be substituted, and two substituents may be combined with each other to form a Spiro structure. Non-limiting examples of a substituted fluorenyl group are shown below. However, embodiments of the present disclosure are not limited thereto:

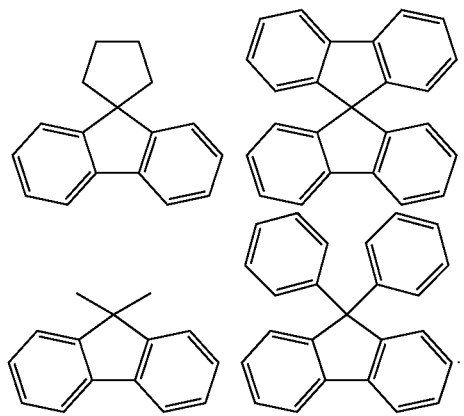

In the present description, the heteroaryl group may be a heteroaryl (e.g., a cyclic aromatic group) including at least one of O, N, P, Si or S as a ring-forming heteroatom. If the heteroaryl group includes two heteroatoms, two heteroatoms may be the same or different. The carbon number for forming a ring of the heteroaryl group may be 2 to 30, for example, 2 to 20. The heteroaryl group may be monocyclic heteroaryl or polycyclic heteroaryl. The polycyclic heteroaryl may have dicyclic or tricyclic structure. Examples of the heteroaryl group may include thiophene, furan, pyrrole, imidazole, thiazole, oxazole, oxadiazole, triazole, pyridine, bipyridine, pyrimidine, triazine, triazole, acridine, pyridazine, pyrazine, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., without limitation.

In the present description, the same explanation of the aryl group may be applied to the arylene group, except that the arylene group is divalent. The same explanation of the heteroaryl group may be applied to the heteroarylene group, except that the heteroarylene group is divalent.

In the present description, the silyl group includes an alkyl silyl group and an aryl silyl group, without limitation. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, an embodiment of the present disclosure is not limited thereto.

In the present description, the carbon number of the amino group (e.g., the number of carbon atoms) is not specifically limited, but may be 1 to 30. The amino group may include an alkyl amino group and an aryl amino group, without limitation. Examples of the amino group include a methylamino group, a dimethylamino group, a phenylamino group, a diphenylamino group, a naphthylamino group, a 9-methyl-anthracenylamino group, a triphenylamino group, etc., without limitation.

In the present description, the carbon number of the carbonyl group is not specifically limited, but may be 1 to 40, 1 to 30, or 1 to 20. For example, the carbonyl group may have the structures below, without limitation:

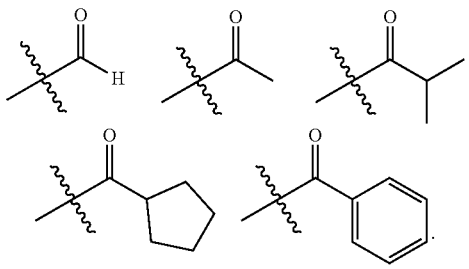

In the description, the carbon numbers of the sulfinyl group and the sulfonyl group are not specifically limited, but may be 1 to 30. The sulfinyl group may include an alkyl sulfinyl group and an aryl sulfinyl group, without limitation. The sulfonyl group may include an alkyl sulfonyl group and an aryl sulfonyl group, without limitation.

In the present description, the thio group may include an alkyl thio group and an aryl thio group, without limitation.

In the present description, the oxy group may include an alkoxy group and an aryloxy group, without limitation. The alkoxy group may be a linear chain, a branched chain or a cyclic chain. The carbon number of the alkoxy group is not specifically limited, but may be, for example, 1 to 20, or 1 to 10. Examples of the oxy group include methoxy, ethoxy, n-propoxy, isopropoxy, butoxy, pentyloxy, hexyloxy, octyloxy, nonyloxy, decyloxy, benzyloxy, etc., without limitation.

In the present description, the boron group includes an alkyl boron group and an aryl boron group, without limitation. Examples of the boron group may include trimethylboron, triethylboron, t-butyldimethylboron, triphenylboron, diphenylboron, phenylboron, etc. However, an embodiment of the present disclosure is not limited thereto.

In the present description, the alkenyl group may be a linear chain or a branched chain. The carbon number is not specifically limited, but may be from 2 to 30, 2 to 20, or 2 to 10. Examples of the alkenyl group may include vinyl, 1-butenyl, 1-pentenyl, 1,3-butadienyl aryl, styrenyl, styrylvinyl, etc. However, an embodiment of the present disclosure is not limited thereto.

In the description, the carbon number of the amine group is not specifically limited, but may be 1 to 30. The amine group may include an alkyl amine group and an aryl amine group, without limitation. Examples of the amine group include a methylamine group, a dimethylamine group, a phenylamine group, a diphenylamine group, a naphthylamine group, a 9-methyl-anthracenylamine group, a triphenylamine group, etc., without limitation.

In the present description, the alkyl group in alkylthio, alkylsulfoxy, alkylaryl, alkylamino, alkylboronyl, alkylsilyl and alkylamine is the same as the above-described alkyl group.

In the present description, the aryl group in aryloxy, arylthio, arylsulfoxy, arylamino, arylboronyl, arylsilyl, and arylamine is the same as the above-described aryl group.

The amine compound according to an embodiment of the present disclosure may be a monoamine compound.

In Formula 1, "c" may be 1. However, an embodiment of the present disclosure is not limited thereto, and "c" may be an integer of 1 to 3.

The amine compound represented by Formula 1 may be represented by the following Formula 2:

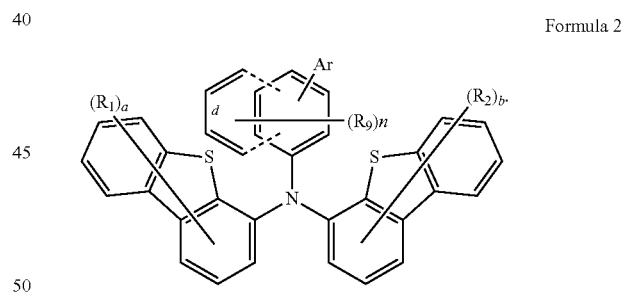

Formula 2

In Formula 2, $R_9$ is hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, "n" is an integer of 0 to 6, and the descriptions of $R_1$, $R_2$, "a", "b", and Ar are the same as those provided in Formula 1.

In Formula 2, "d" is 0 or 1. If "d" is 0, Formula 2 corresponds to Formula 1 where L is a phenylene group. If "d" is 1, Formula 2 corresponds to Formula 1 where L is a naphthylene group.

In Formula 2, if "n" is 1, $R_9$ may not be hydrogen, and if "n" is 2 or more, a plurality of $R_9$ groups are the same or different.

The amine compound represented by Formula 2 may be represented by one of the following Formula 2-1 to Formula 2-3:

Formula 2-1

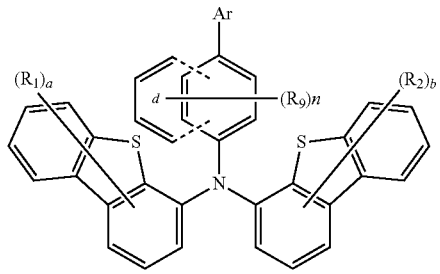

Formula 2-2

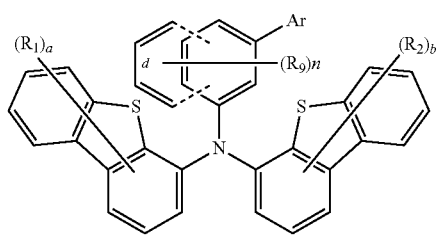

Formula 2-3

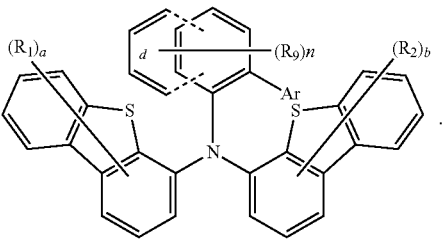

In Formula 2-1 to Formula 2-3, $R_1$, $R_2$, $R_9$, "a", "b", "n", Ar and "d" are the same as defined above.

The amine compound represented by Formula 2-1 may be represented by the following Formula 2-1-1 or Formula 2-1-2:

Formula 2-1-1

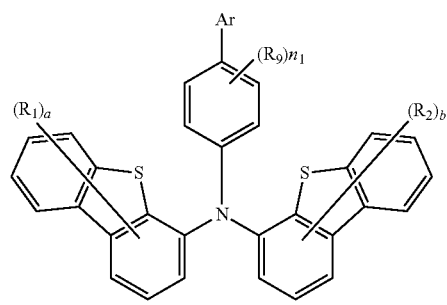

Formula 2-1-2

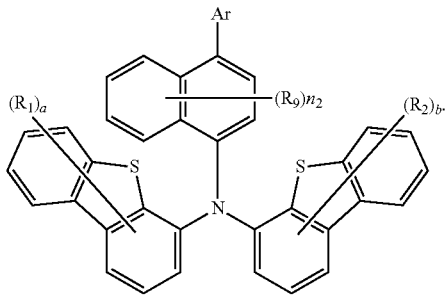

In Formula 2-1-1 and 2-1-2, "n1" is an integer of 0 to 4, "n2" is an integer of 0 to 6, and $R_1$, $R_2$, $R_g$, "a", "b", and Ar are the same as defined above.

The amine compound represented by Formula 2-2 may be represented by the following Formula 2-2-1 or Formula 2-2-2:

Formula 2-2-1

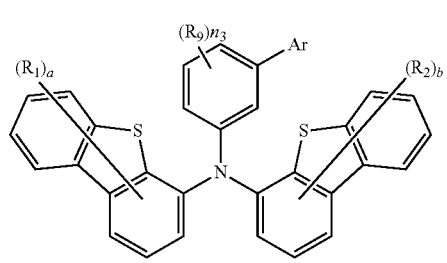

Formula 2-2-2

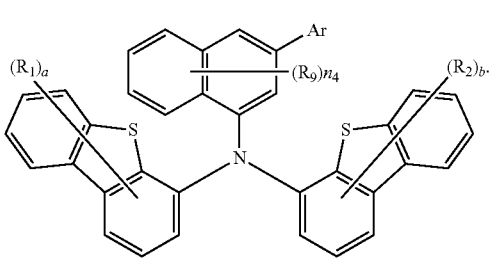

In Formula 2-2-1 and 2-2-2, "n3" is an integer of 0 to 4, "n4" is an integer of 0 to 6, and $R_1$, $R_2$, $R_9$, "a", "b", and Ar are the same as defined above.

The amine compound represented by Formula 2-3 may be represented by the following Formula 2-3-1 or Formula 2-3-2:

Formula 2-3-1

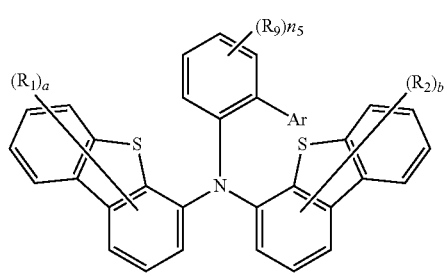

-continued

Formula 2-3-2

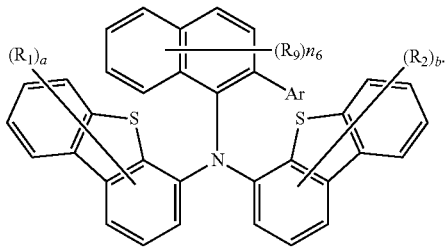

In Formula 2-3-1 and 2-3-2, "n5" is an integer of 0 to 4, "n6" is an integer of 0 to 6, and $R_1$, $R_2$, $R_9$, "a", "b", and Ar are the same as defined above.

The amine compound represented by Formula 1 may be represented by one of the following Formulae 3-1 to 3-3:

Formula 3-1

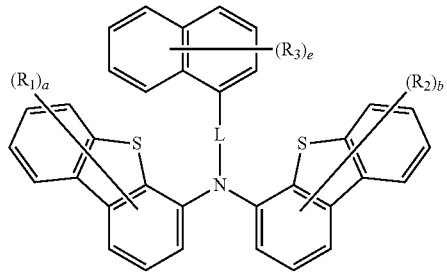

Formula 3-2

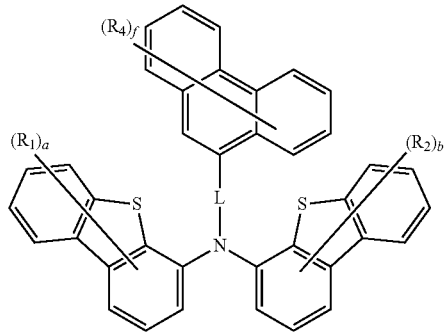

Formula 3-3

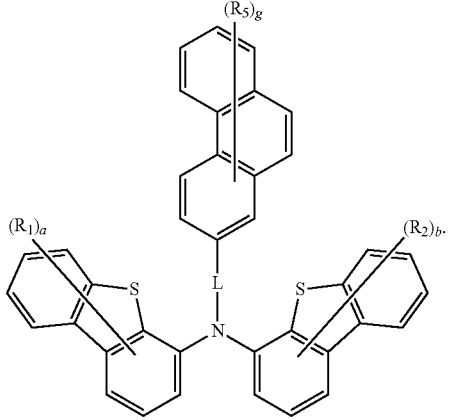

In Formulae 3-1 to 3-3, $R_3$ to $R_5$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, $R_3$ to $R_5$ may be each independently a substituted or unsubstituted phenyl group or a substituted or unsubstituted naphthyl group.

"e" may be an integer of 0 to 7. If "e" is 0, the amine compound represented by Formula 3-1 may not be substituted with $R_3$. If "e" is an integer of 2 or more, a plurality of $R_3$ groups may be the same or different.

"f" and "g" may be each independently an integer of 0 to 9. If "f" is 0, the amine compound represented by Formula 3-2 may not be substituted with $R_4$. If "f" is an integer of 2 or more, a plurality of $R_4$ groups may be the same or different. If "g" is 0, the amine compound represented by Formula 3-3 may not be substituted with $R_5$. If "g" is an integer of 2 or more, a plurality of $R_5$ groups may be the same or different.

The amine compound represented by Formula 1 may be represented by the following Formula 4:

Formula 4

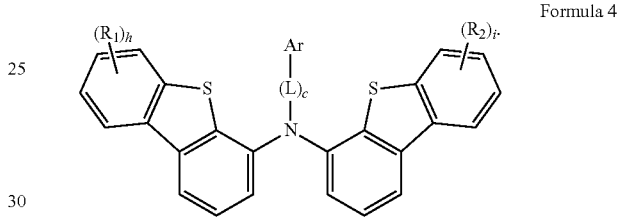

In Formula 4, "h" and "i" are each independently an integer of 0 to 2, at least one of "h" or "i" is 1 or 2, and Ar, L and "c" are the same as defined above.

The amine compound represented by Formula 1 may be represented by the following Formula 5:

Formula 5

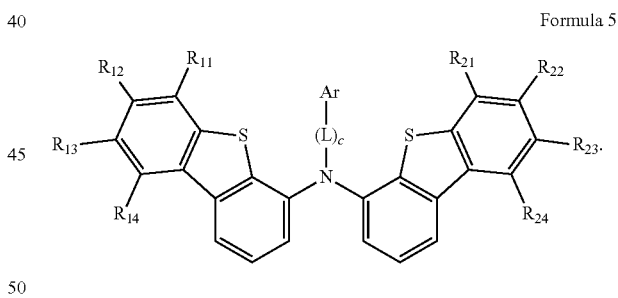

In Formula 5, Ar, L and "c" are the same as defined above.

In Formula 5, $R_{11}$ to $R_{14}$ and $R_{21}$ to $R_{24}$ may be each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. In some embodiments, at least one of $R_{11}$ to $R_{14}$ and $R_{21}$ to $R_{24}$ may be deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, at least one of $R_{11}$ to $R_{14}$, and $R_{21}$ to $R_{24}$ may be a substituted or unsubstituted aryl group having 6 to 30 carbon atoms for forming a ring, or a substituted or unsubstituted heteroaryl group having 2 to 30 carbon atoms for forming a ring.

Two members in at least one group selected from $R_{11}$ and $R_{21}$, $R_{12}$ and $R_{22}$, $R_{13}$ and $R_{23}$, and $R_{14}$ and $R_{24}$ may be different. For example, $R_{11}$ may be a substituted or unsubstituted phenyl group, or a substituted or unsubstituted naphthyl group, and $R_{21}$ may be hydrogen. In an embodiment, $R_{12}$ may be a fluorine atom, or a chlorine atom, and $R_{22}$ may be hydrogen. In an embodiment, $R_{13}$ may be a substituted or unsubstituted ethyl group, and $R_{23}$ may be hydrogen. In other words, if $R_{11}$ to $R_{14}$ are substituents on one dibenzothiophene moiety of Formula 5, and $R_{21}$ to $R_{24}$ are substituents on another dibenzothiophene moiety of Formula 2, different substituents are substituted at specific carbon positions so as to form an asymmetric structure with a nitrogen atom as the center.

The amine compound represented by Formula 1 may be represented by the following Formula 6:

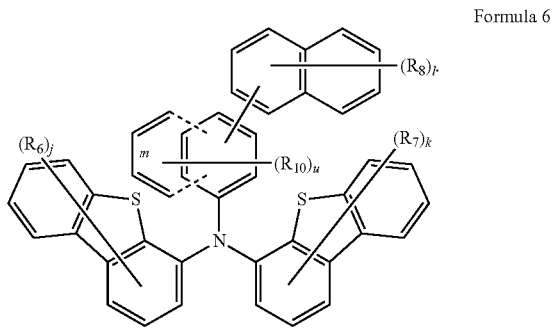

Formula 6

In Formula 6, $R_6$, $R_7$ and $R_{10}$ may be each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. $R_6$ and $R_7$ may be each independently deuterium, a halogen atom, a substituted or unsubstituted alkyl group having 1 to 10 carbon atoms, a substituted or unsubstituted phenyl group, a substituted or unsubstituted naphthyl group, a substituted or unsubstituted phenanthryl group, a substituted or unsubstituted carbazolyl group, a substituted or unsubstituted dibenzofuranyl group, or a substituted or unsubstituted dibenzothiophenyl group.

In Formula 6, "j" and "k" may be each independently an integer of 0 to 7, "l" may be an integer of 0 to 7, "m" may be 0 or 1, and "u" may be an integer of 0 to 6. If "j" is 1, $R_6$ may not be hydrogen, and if "j" is 2 or more, a plurality of $R_6$ groups are the same or different. If "k" is 1, $R_7$ may not be hydrogen, and if "k" is 2 or more, a plurality of $R_7$ groups are the same or different. If "l" is 1, $R_8$ may not be hydrogen, and if "l" is 2 or more, a plurality of $R_8$ groups are the same or different. If "u" is 1, $R_{10}$ may not be hydrogen, and if "u" is 2 or more, a plurality of $R_{10}$ groups are the same or different.

In Formula 6, $R_8$ may be hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. $R_8$ may be a substituted or unsubstituted phenyl group, or a substituted or unsubstituted naphthyl group. In some embodiments, $R_8$ may be connected with an adjacent group to form a ring. For example, in the amine compound represented by Formula 6, a naphthyl group may be substituted with two $R_8$ groups, and the two substituted $R_8$ groups may be connected with each other to form a six-member aromatic ring. In case of the formation of the six-member aromatic ring via the connection of two $R_8$ groups, a phenanthryl group may be connected with an amine core via a phenylene linker (e.g., if "m" is 0) or a naphthylene linker (e.g., is "m" is 1) in the amine compound represented by Formula 6.

The amine compound represented by Formula 1 may be at least one selected from the compounds represented in Compound Group 1. However, an embodiment of the present disclosure is not limited thereto.

Compound Group 1

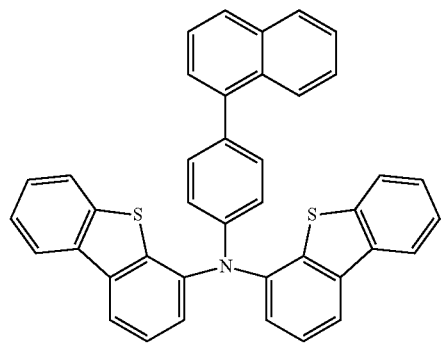

1

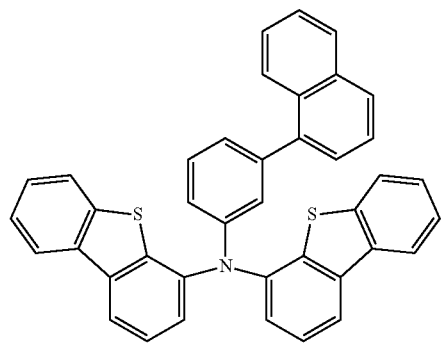

2

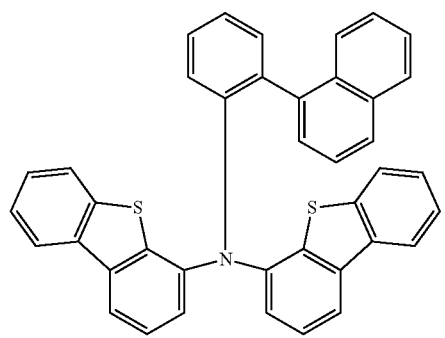

3

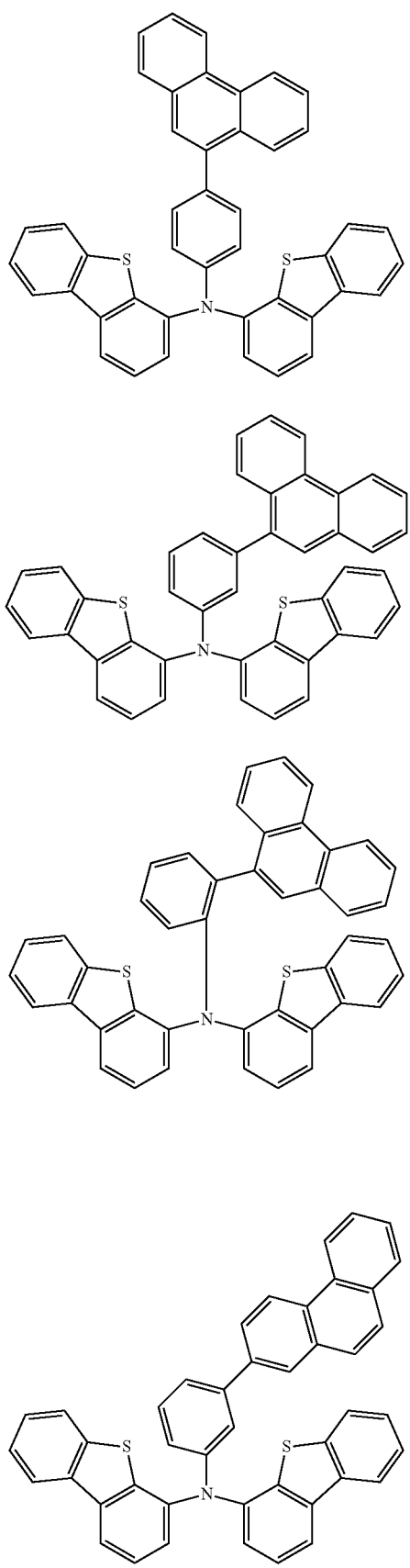
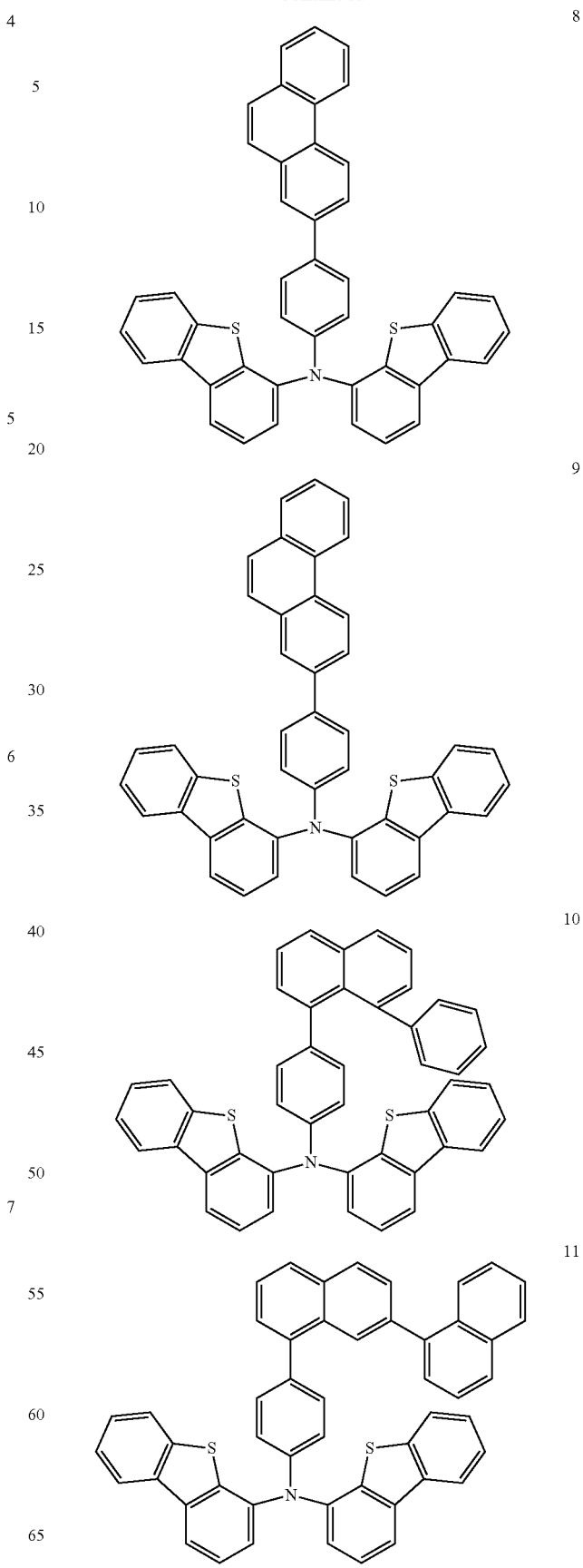

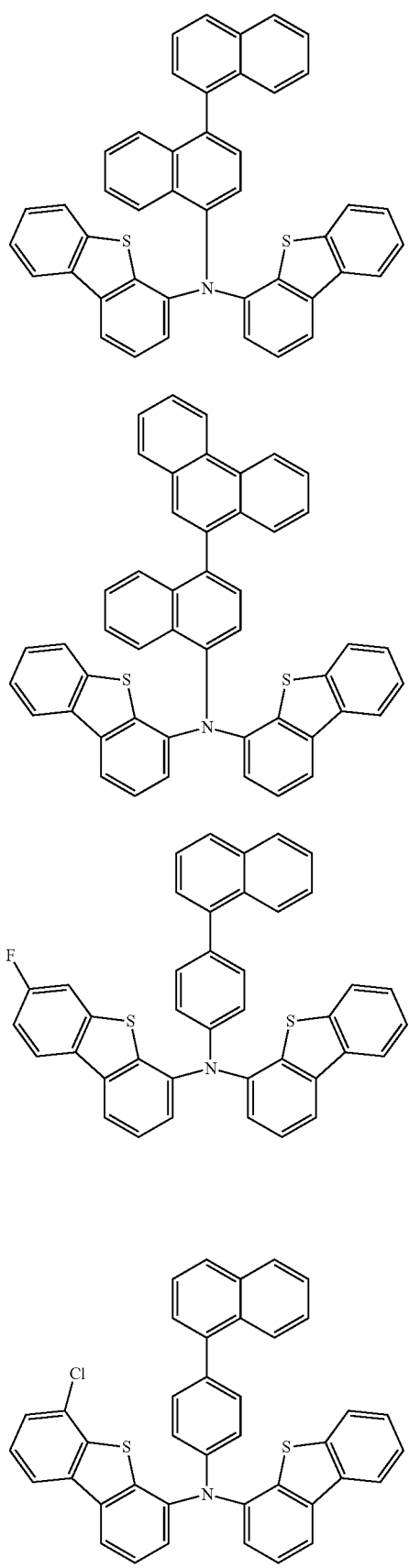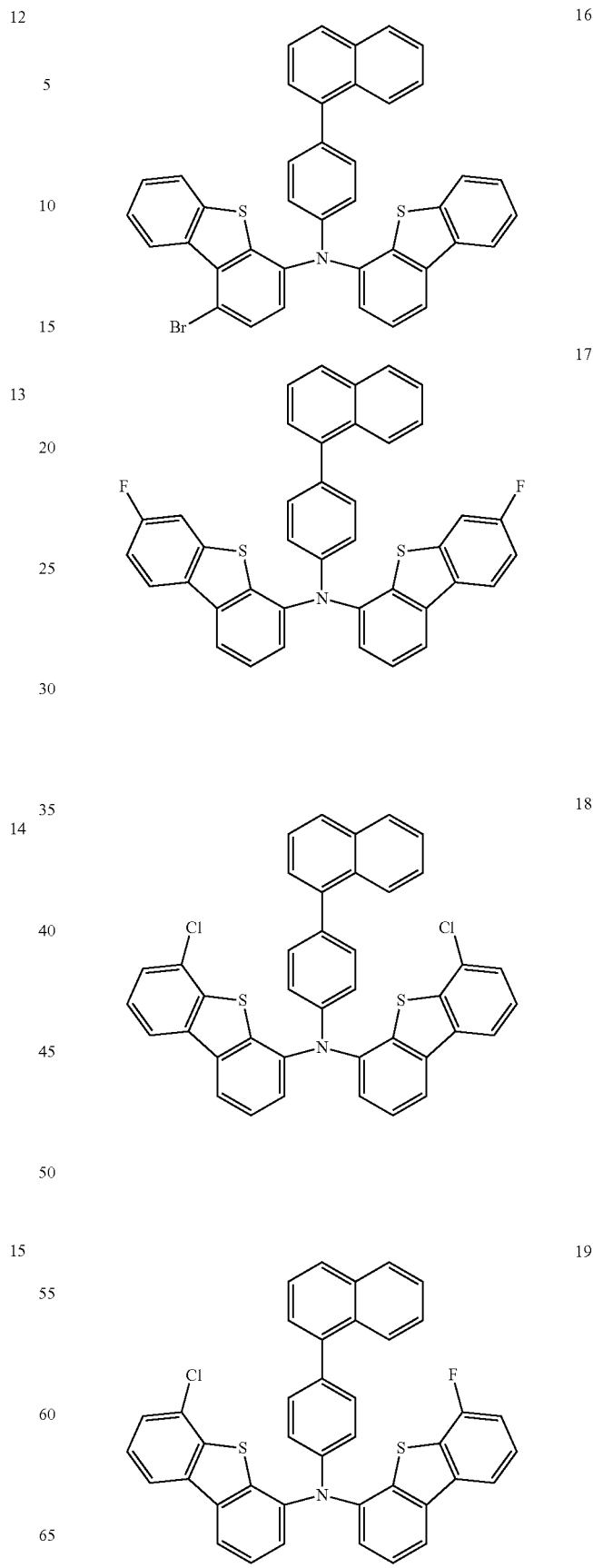

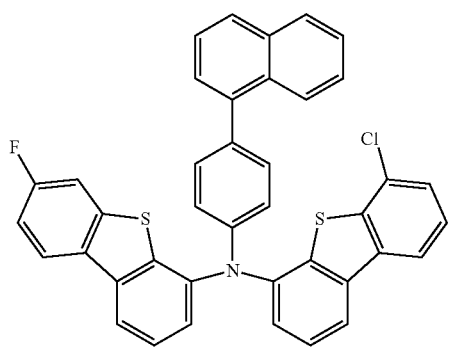
20
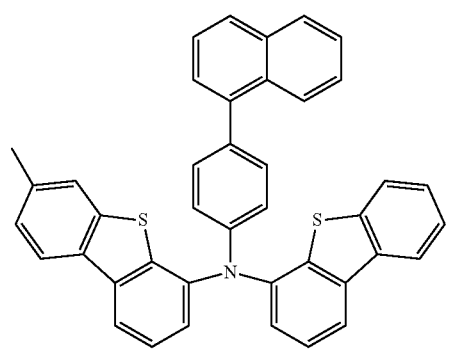
21
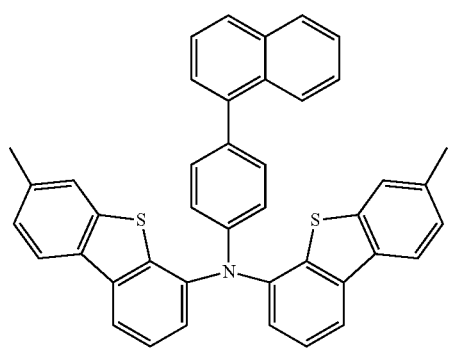
22
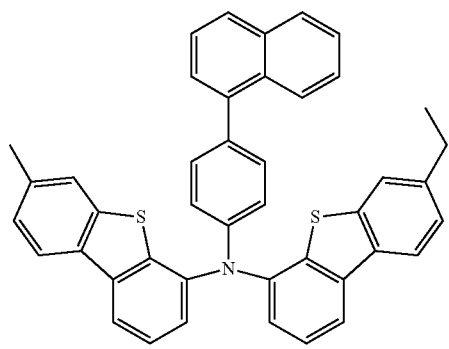
23
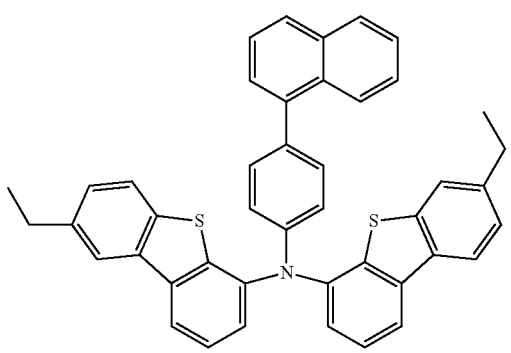
24
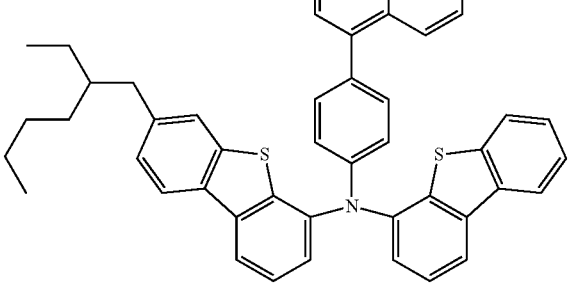
25
26
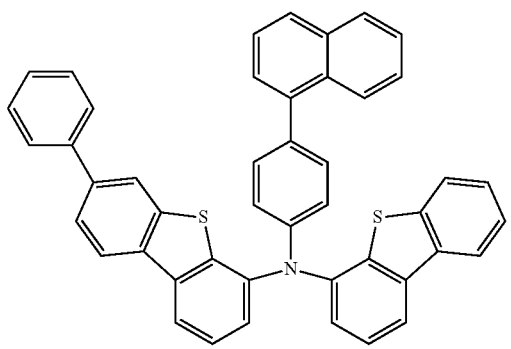
27

28
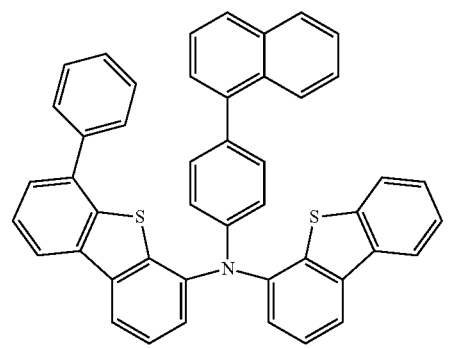
29
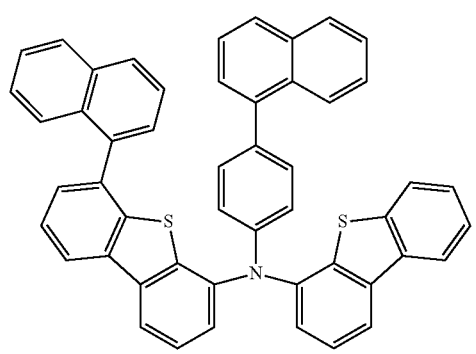
30
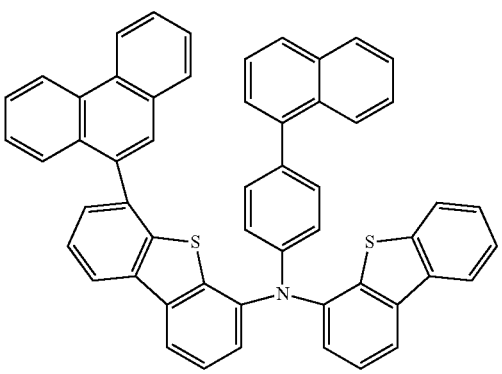
31
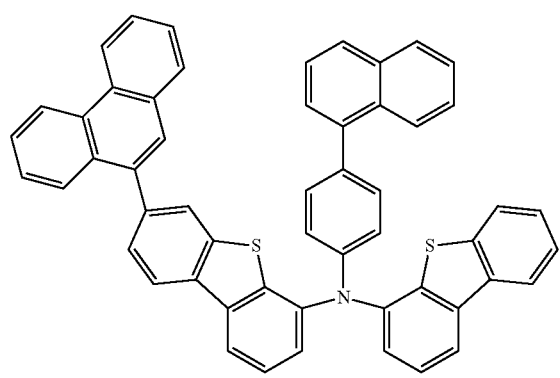
32
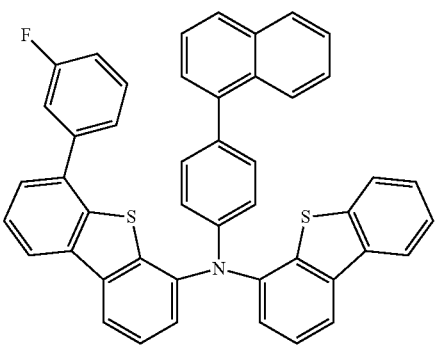
33
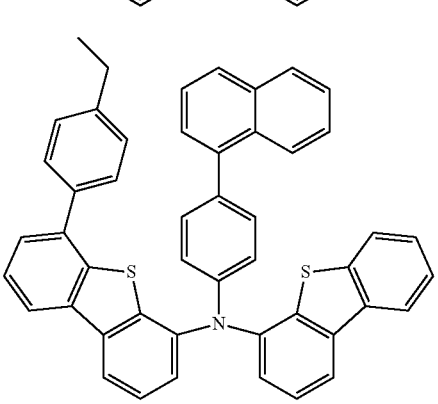
34
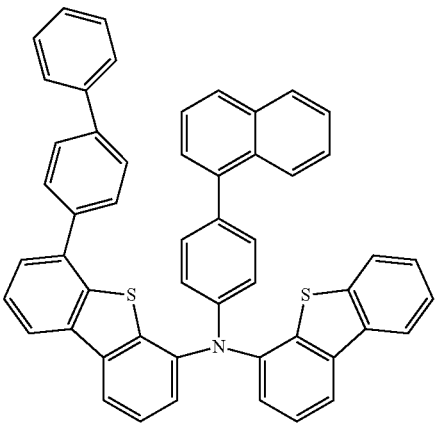
35
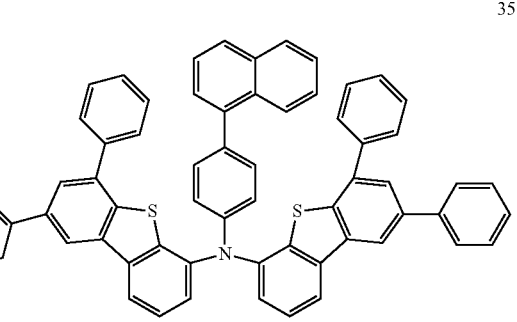

36
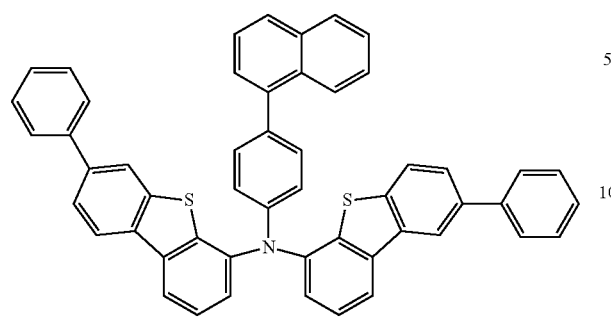
37
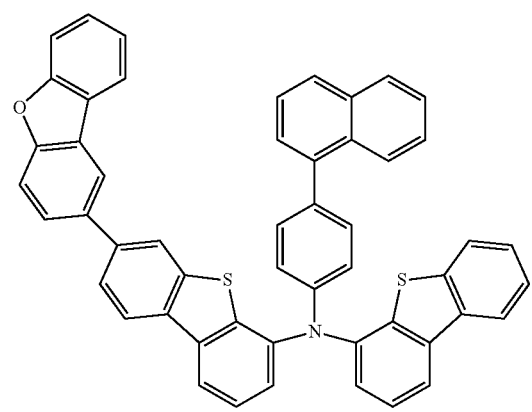
38
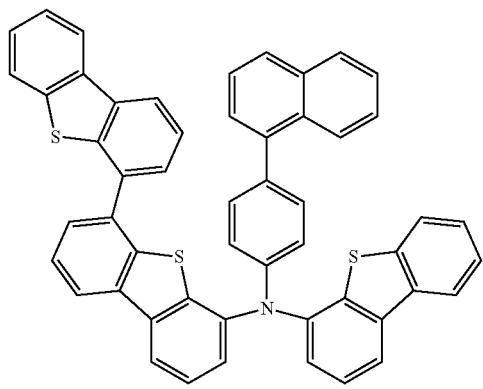
39
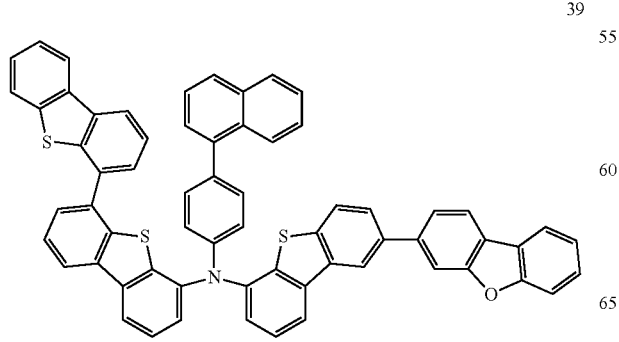
40
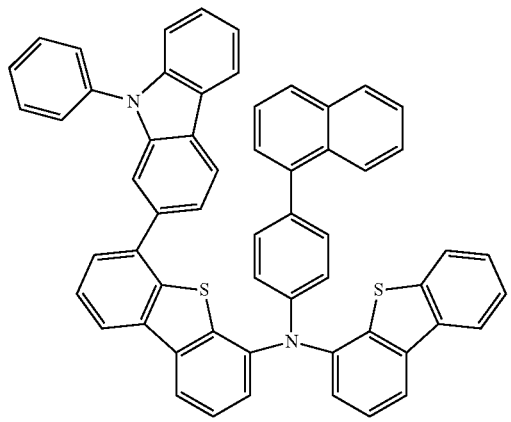
41
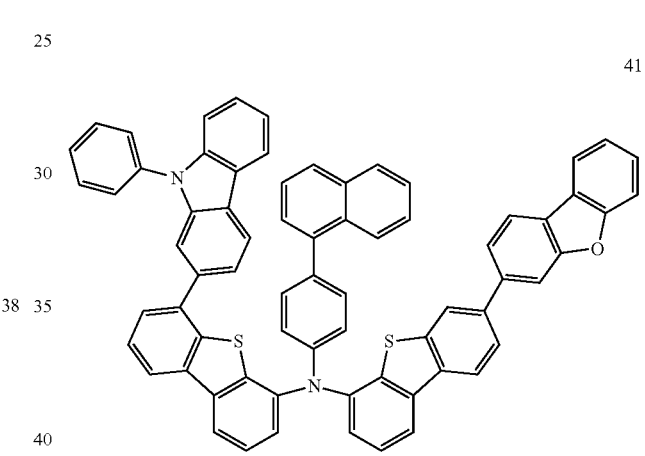
42
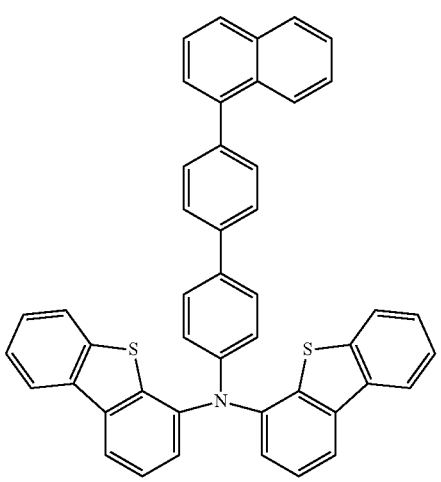

43
44
45
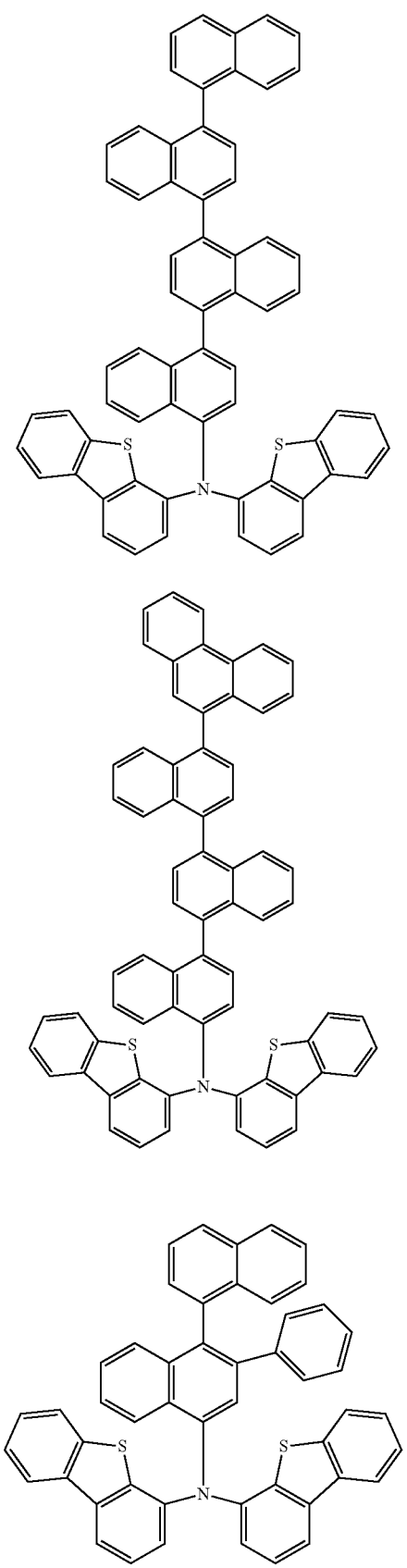
46
47

48

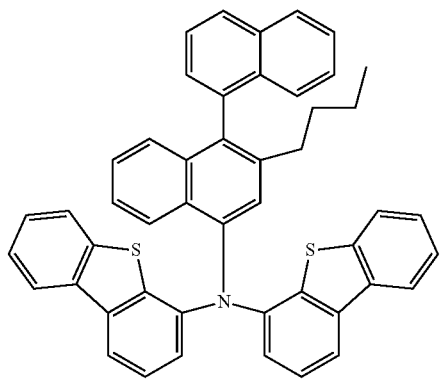

49

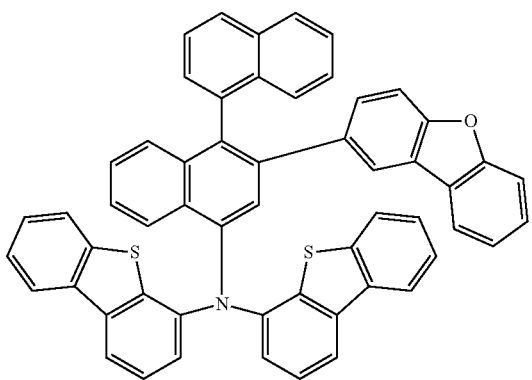

50

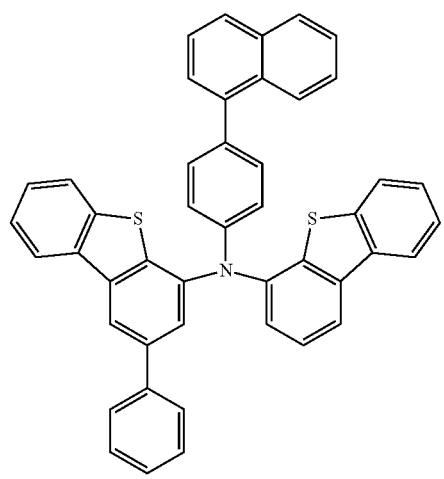

51

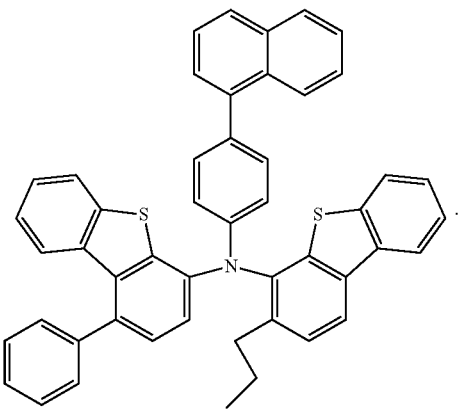

Referring to Formula 1 or Formula 6, the amine compound according to an embodiment of the present disclosure includes two dibenzothiophene groups which are directly bonded to an amine core at the carbon position number of 4 of each dibenzothiophene group (e.g., as illustrated in Formulae 1 and 6). In addition, at the amine core, an aryl substituent having 10 or more carbon atoms (e.g., as represented by Ar) is substituted via a linker such as a phenylene group or a naphthylene group (e.g., as represented by L).

If the amine compound represented by Formula 1 or Formula 6 is applied to an organic electroluminescence device, high emission efficiency and long life may be secured. The amine compound represented by Formula 1 or Formula 6 includes two dibenzothiophene groups which are connected with the amine core (e.g., to the N atom of the amine group) at each carbon position number of 4 (e.g., as illustrated in Formulae 1 and 6), and high amorphous properties may be attained. Thus, if the amine compound represented by Formula 1 or Formula 6 is applied to an organic electroluminescence device, high emission efficiency and long life may be accomplished. In addition, the phenyl group or the naphthyl group which is connected with the amine core is protected through the aryl substituent having 10 or more carbon atoms, and the decomposition of the amine compound may be restrained (e.g., reduced) during the driving of a device. Thus, emission efficiency may be maintained high and the life of a device may be increased.

Referring to FIG. 1 and FIG. 2, an organic electroluminescence device according to an embodiment of the present disclosure will be explained. An emission layer EML may include the amine compound according to an embodiment of the present disclosure. In some embodiments, a hole transport region HTR may include the amine compound represented by Formula 1.

Hereinafter, the above-described amine compound according to an embodiment of the present disclosure will be explained mainly with respect to the different features, as compared to the previously described embodiment, and unexplained parts will follow the above explanation on the amine compound according to an embodiment of the present disclosure.

The first electrode EL1 has conductivity. The first electrode EU may be a pixel electrode or an anode. The first electrode EL1 may be a transmissive electrode, a transflective electrode, or a reflective electrode. If the first electrode EU is the transmissive electrode, the first electrode EL1 may be formed using a transparent metal oxide such as indium tin oxide (ITO), indium zinc oxide (IZO), zinc oxide (ZnO), and/or indium tin zinc oxide (ITZO). If the first electrode EU1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transfiective layer formed using any of the above materials, or a transparent layer formed using ITO, IZO, ZnO, and/or ITZO.

Hereinafter, a case where the amine compound according to an embodiment of the present disclosure is included in a hole transport region HTR will be explained. However, an embodiment of the present disclosure is not limited thereto. The amine compound according to an embodiment of the present disclosure may be included in at least one layer among one or more organic layers disposed between the first electrode EL1 and the second electrode EL2. For example, the amine compound according to an embodiment of the present disclosure may be included in an emission layer EML.

As described above, an organic electroluminescence device 10 according to an embodiment of the present disclosure may include the amine compound according to an embodiment of the present disclosure in a hole transport region HTR.

The hole transport region HTR may include the amine compound represented by Formula 6.

The hole transport region HTR is provided on the first electrode EL1. The hole transport region HTR may include at least one of a hole injection layer HIL, a hole transport layer HTL, a hole buffer layer, or an electron blocking layer.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL, or a hole transport layer HTL, and may have a structure of a single layer formed using a hole injection material and a hole transport material. In some embodiments, the hole transport region HTR may have a structure of a single layer formed using a plurality of different materials, or a structure (laminated from the first electrode EL1) of hole injection layer HIL/hole transport layer HTL, hole injection layer HIL/hole transport layer HTL/hole buffer layer, hole injection layer HIL/hole buffer layer, hole transport layer HTL/ hole buffer layer, or hole injection layer HIL/hole transport layer HTL/electron blocking layer, without limitation.

The hole transport region HTR may be formed using various methods such as a vacuum deposition method, a spin coating method, a cast method, a Langmuir-Blodgett (LB) method, an inkjet printing method, a laser printing method, and/or a laser induced thermal imaging (LITI) method.

The hole transport region HTR may include the amine compound according to an embodiment of the present disclosure. The hole transport region HTR may include the amine compound according to an embodiment of the present disclosure as a hole transport material. If the hole transport region HTR includes a plurality of layers, the amine compound of an embodiment may be included in a layer which contacts the emission layer EML among the plurality of layers. For example, if the hole transport region HTR is composed of a hole injection layer HIL and a hole transport layer HTL, as shown in FIG. 2, the amine compound according to an embodiment of the present disclosure may be included in the hole transport layer HTL.

If the hole transport layer HTL includes the amine compound according to an embodiment of the present disclosure, the hole injection layer HIL may include, for example, a phthalocyanine compound (such as copper phthalocyanine), N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4',4"-tris(N,N-diphenylamino)triphenylamine (TDATA), 4,4',4"-tris{N-(1-naphthyl)-N-phenylamino}-triphenylamine (1-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthyl)-N,N'-diphenyl-(1, 1'-biphenyl)-4,4'-diamine (NPD), triphenylamine-containing polyether ketone (TPAPEK), 4-isopropyl-4'-methyldiphenyliodonium tetrakis(pentafluorophenyl)borate, tetrakis(pentafluorophenyl)borate, 1,4,5,8,9,11-hexaazatriphenylenehexacarbonitrile (HAT-CN), etc., without limitation.

The hole transport layer HTL may further include any known (e.g., suitable) material in addition to the amine compound according to an embodiment of the present disclosure. The hole transport layer HTL may include, for example, carbazole derivatives (such as N-phenyl carbazole, polyvinyl carbazole, and/or 1,3-bis(N-carbazolyl)benzene (mCP)), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthyl)-N, N'-diphenyl-(1,1'-biphenyl)-4,4'-diamine (NPD), 4,4'-cyclohexylidene bis[N,N-bis(4-methylpheny)benzenamine] (TAPC), 4,4'-bis[N,N'-(3-tolyl)amino]-3,3'-dimethylbiphenyl (HMTPD), etc., without limitation.

The thickness of the hole transport region HTR may be from about 150 Å to about 12,000 Å, for example, from about 150 Å to about 1,500 Å. If the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 50 Å to about 1,000 Å. If the thicknesses of the hole transport region HTR, the hole injection layer HIL, and the hole transport layer HTL satisfy any of the above-described ranges, satisfactory (or suitable) hole transport properties may be obtained without substantial increase of a driving voltage.

The hole transport region HTR may further include a charge generating material, in addition to the above-described materials, to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without limitation. For example, non-limiting examples of the p-dopant may include quinone derivatives (such as tetracyanoquinodimethane (TCNQ) and/or 2,3,5,6-tetrafluoro-tetracyanoquinodimethane (F4-TCNQ)), and metal oxides (such as tungsten oxide and/or molybdenum oxide), without limitation.

As described above, the hole transport region HTR may further include at least one of a hole buffer layer or an electron blocking layer, in addition to the hole injection layer HIL and the hole transport layer HTL. The hole buffer layer may compensate a resonance distance according to the wavelength of light emitted from the emission layer EML and increase light emission efficiency. Any of the materials included in the hole transport region HTR may be used as materials included in the hole buffer layer. The electron blocking layer is a layer configured to prevent or reduce the electron injection from the electron transport region ETR to the hole transport region HTR.

The emission layer EML is provided on the hole transport region HTR. The emission layer EML is disposed on the hole transport layer HTL and may make contact (e.g., may be in contact) with the hole transport layer HTL. The thickness of the emission layer EML may be, for example, from about 100 Å to about 600 Å. The emission layer EML may have a single layer formed using a single material, a single layer formed using a plurality of different materials, or a multilayer structure having a plurality of layers formed using a plurality of different materials.

The emission layer EML may emit one of red light, green light, blue light, white light, yellow light, or cyan light. The emission layer EML may include a fluorescence material or a phosphorescence material. For example, the emission layer EML may include a thermally activated delayed fluorescence (TADF) material.

The emission layer EML may include a host and a dopant.

The host material of the emission layer EML may be selected from anthracene derivatives, fluoranthene derivatives, pyrene derivatives, arylacetylene derivatives, fluorene derivatives, perylene derivatives, chrysene derivatives and phenanthrene derivatives, for example, pyrene derivatives, perylene derivatives, chrysene derivatives, phenanthrene derivatives, and anthracene derivatives. For example, as the host material of the emission layer EML, anthracene derivatives represented by the following Formula 7 may be used:

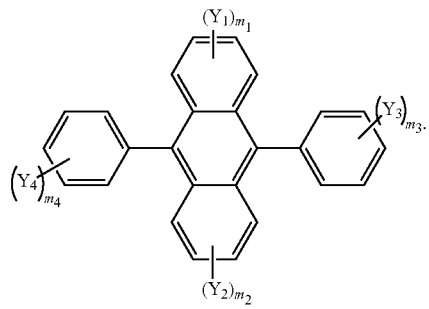

Formula 7

In Formula 7, $Y_1$ to $Y_4$ may be each independently hydrogen, deuterium, a halogen atom, a substituted or unsubstituted silyl group, a substituted or unsubstituted alkyl group having 1 to 15 carbon atoms, a substituted or unsubstituted aryl group having 6 to 30 carbon atoms for forming a ring, or a substituted or unsubstituted heteroaryl group having 2 to 30 carbon atoms for forming a ring, $m_1$ and $m_2$ may be each independently an integer of 0 to 4, $m_3$ and $m_4$ may be each independently an integer of 0 to 5. In Formula 7, $Y_3$ and $Y_4$ may be each independently combined with an adjacent group to form a ring.

The compound represented by Formula 7 may include, for example, the compounds represented by the structures below. However, the compound represented by Formula 7 is not limited to the following structures.

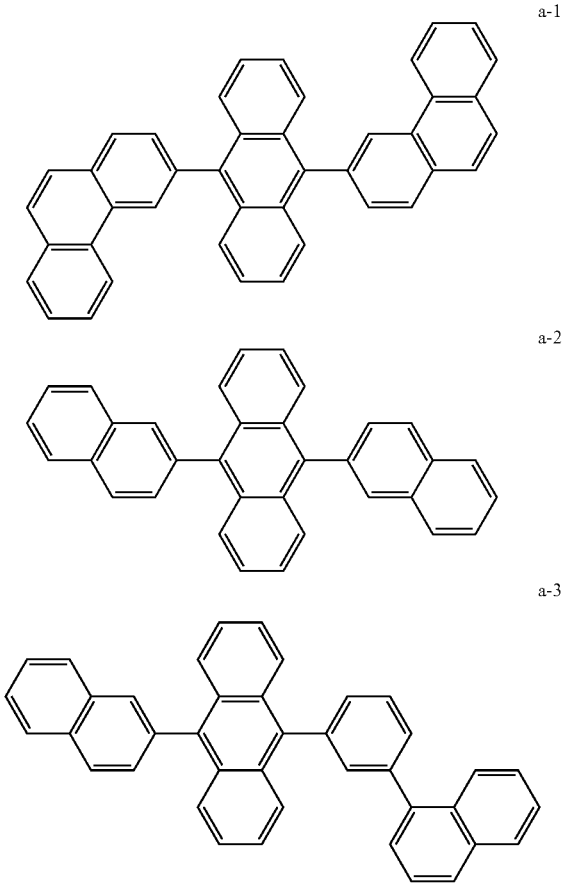

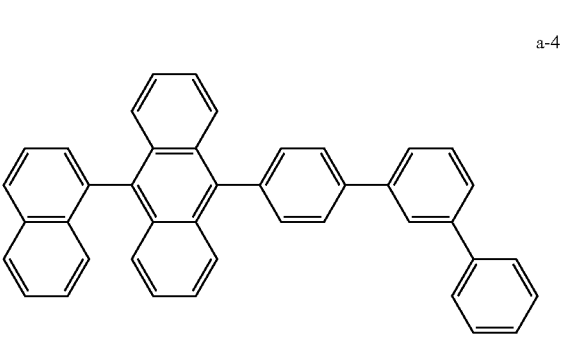

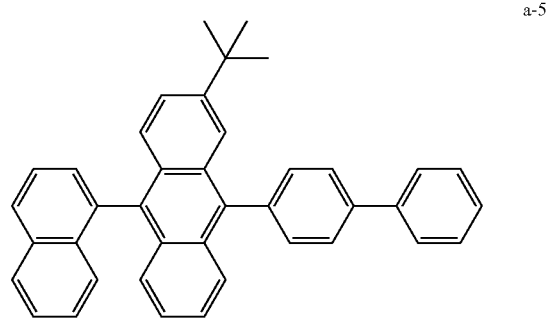

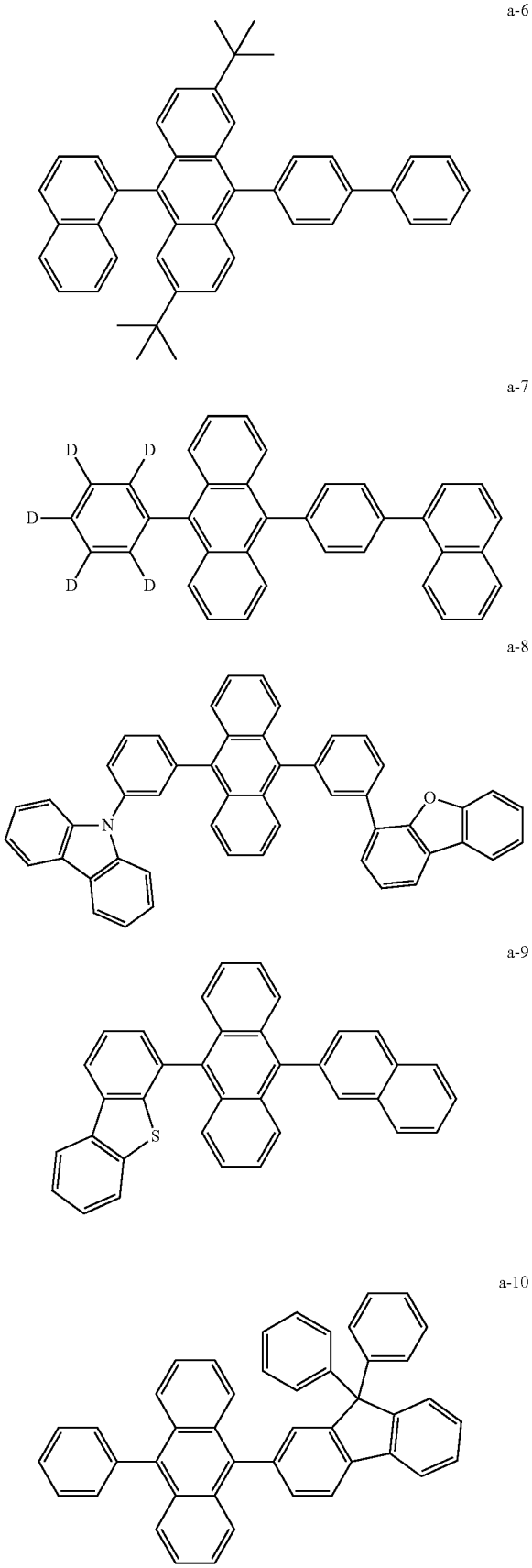

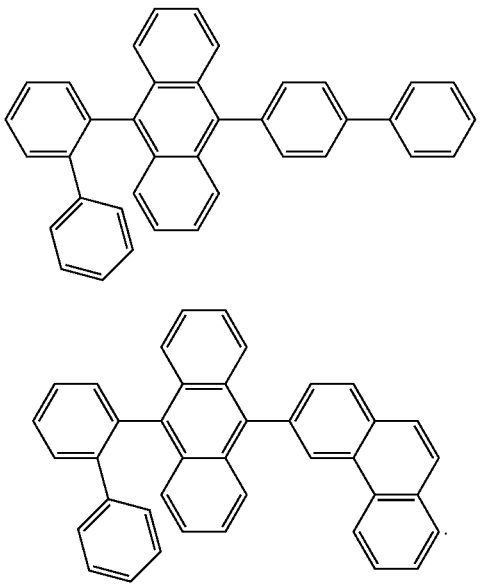

The host is not specifically limited and may include, for example, tris(8-hydroxyquinolino)aluminum (Alq₃), 4,4'-bis (N-carbazolyl)-1,1'-biphenyl (CBP), poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), etc.

The dopant may be, for example, styryl derivatives (for example, 1,4-bis[2-(3-N-ethylcarbazoryl)vinyl]benzene (BCzVB), 4-(di-p-tolylamino)-4'-[(di-p-tolylamino)styryl] stilbene (DPAVB), and/or N-(4-((E)-2-(6-((E)-4-(diphenylamino)styryl)naphthalen-2-yl)vinyl)phenyl)-N-phenylbenzenamine (N-BDAVBi), perylene and the derivatives thereof (for example, 2,5,8,11-tetra-t-butylperylene (TBP)), pyrene and the derivatives thereof (for example, 1,1-dipyrene, 1,4-dipyrenylbenzene, and/or 1,4-bis(N,N-diphenylamino)pyrene), etc. The dopant may be also 10-phenyl-10H,10'H-spiro[acridine-9,9'-anthracen]-10'-one.

If the emission layer EML emits red light, the emission layer EML may further include a fluorescence material including tris(dibenzoylmethanato)phenanthroline europium (PBD:Eu(DBM)3(Phen)) and/or perylene. If the emission layer EML emits red color, the dopant included in the emission layer EML may be selected from, for example, a metal complex or an organometallic complex such as bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr) and octaethylporphyrin platinum (PtOEP), rubrene and the derivatives thereof, and 4-dicyanomethylene-2-(p-dimethylaminostyryl)-6-methyl-4H-pyrane (DCM) and the derivatives thereof.

If the emission layer EML emits green light, the emission layer EML may further include a fluorescence material including tris(8-hydroxyquinolino)aluminum (Alq₃). If the emission layer EML emits green light, the dopant included in the emission layer EML may be selected from, for example, a metal complex or an organometallic complex such as fac-tris(2-phenylpyridine)iridium (Ir(ppy)$_3$), and coumarin and the derivatives thereof.

If the emission layer EML emits blue light, the emission layer EML may further include a fluorescence material including, for example, any one selected from the group consisting of spiro-DPVBi, spiro-6P, distyryl-benzene (DSB), distyryl-arylene (DSA), a polyfluorene (PFO)-based polymer and a poly(p-phenylene vinylene (PPV)-based polymer. If the emission layer EML emits blue light, the dopant included in the emission layer EML may be selected from a metal complex or an organometallic complex such as (4,6-F2ppy)$_2$Irpic, and perylene and the derivatives thereof.

The electron transport region ETR is disposed on the emission layer EML. The electron transport region ETR may include at least one of a hole blocking layer, an electron transport layer ETL or an electron injection layer EIL. However, an embodiment of the present disclosure is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In some embodiments, the electron transport region ETR may have a single layer structure having a plurality of different materials, or a structure, laminated from the first electrode EL1, of electron transport layer ETL/electron injection layer EIL, or hole blocking layer/electron transport layer ETL/electron injection layer EIL, without limitation.

The electron transport region ETR may be formed using various methods such as a vacuum deposition method, a spin coating method, a cast method, a Langmuir-Blodgett (LB) method, an inkjet printing method, a laser printing method, and/or a laser induced thermal imaging (LITI) method.

The electron transport layer ETL may include, for example, tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl)anthracene (ADN), bis[2-(diphenylphosphino)phenyl]ether oxide (DPEPO), or a mixture thereof, without limitation. The thickness of the electron transport layer ETL may be from about 100 Å to about 1,000 Å, for example, from about 150 Å to about 500 Å. If the thickness of the electron transport layer ETL satisfies the above-described range, satisfactory (or suitable) electron transport properties may be obtained without substantial increase of a driving voltage.

If the electron transport region ETR includes the electron injection layer EIL, a metal such as Al, Ag, Li, Mg and/or Ca, or a mixture thereof, may be included. However, an embodiment of the present disclosure is not limited thereto. For example, the electron injection layer EIL may use LiF, lithium quinolate (LiQ), Li$_2$O, BaO, NaCl, CsF, a metal in lanthanoides such as Yb, or a metal halide such as RbCl, and RbI. However, an embodiment of the present disclosure is not limited thereto. The electron injection layer EIL also may be formed using a mixture material of an electron transport material and an insulating organo metal salt. The organo metal salt may be a material having an energy band gap of about 4 eV or more. In some embodiments, the organo metal salt may include, for example, metal acetates, metal benzoates, metal acetoacetates, metal acetylacetonates, and/or metal stearates. The thickness of the electron injection layer EIL may be from about 10 Å to about 100 Å. If the thickness of the electron injection layer EIL satisfies the above-described range, satisfactory electron transport properties may be obtained without substantial increase of a driving voltage.

The electron transport region ETR may include a hole blocking layer as described above. The hole blocking layer may include, for example, at least one of 2,9-dimethyl-4,7-diphenyl-1,10-phenanthroline (BCP), or 4,7-diphenyl-1,10-phenanthroline (Bphen). However, an embodiment of the present disclosure is not limited thereto.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using any of the above-described materials and a transparent conductive layer formed using ITO, IZO, ZnO, ITZO, etc., without limitation.

Though not shown, the second electrode EL2 may be connected (e.g., coupled) with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

If the organic electroluminescence device 10 is a top emission type (e.g., top emission organic electroluminescence device), the first electrode EL1 may be a reflective electrode and the second electrode EL2 may be a transmissive electrode or a transflective electrode. If the organic electroluminescence device 10 is a bottom emission type (e.g., bottom emission organic electroluminescence device), the first electrode EL1 may be a transmissive electrode or a transflective electrode and the second electrode EL2 may be a reflective electrode.

The organic electroluminescence device according to an embodiment of the present disclosure includes the amine compound represented by Formula 1 or Formula 6, and high emission efficiency and long life may be secured. The amine compound according to an embodiment of the present disclosure may be used as the hole transport material, and the high emission efficiency and the long life of the organic electroluminescence device may be accomplished. For example, the amine compound represented by Formula 1 or Formula 6 includes two dibenzothiophene groups which are bonded to an amine core at each carbon position number of 4 (as shown in Formulae 1 and 6, for example), and the resulting organic electroluminescence device may have high amorphous properties, high hole transport properties, and high emission efficiency and long life. In addition, a divalent phenyl group or a naphthyl group, which is connected to an amine core, is protected by an aryl substituent having 10 or more carbon atoms, and the decomposition of the amine compound during the driving of a device may be restrained (or reduced), emission efficiency may be maintained high, and the life of the device may increase.

Hereinafter, the present disclosure will be explained in more detail with reference to particular preparation methods, embodiments and comparative embodiments. The following embodiments are only illustrations provided to assist the understanding of the present disclosure, and the scope of the present disclosure is not limited thereto.

The amine compounds according to example embodiments of the present disclosure may be synthesized, for example, as follows. However, an embodiment of the present disclosure is not limited thereto.

1. Synthesis of Compound 1

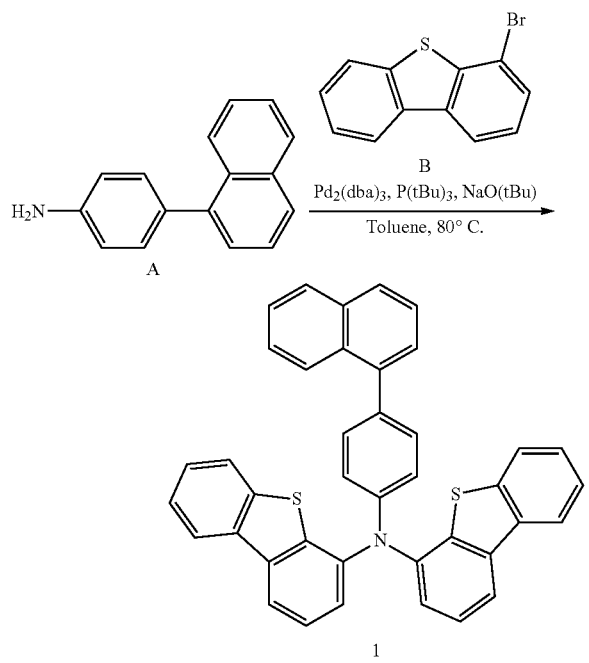

A toluene suspension (1150 ml) of Compound A (14.0 g, 63.9 mmol), Compound B (33.6 g, 127.7 mmol), tris(dibenzylideneacetone)dipalladium(0) (5.8 g, 6.4 mmol), tri-tert-butylphosphine (2.1 g, 10.2 mmol), and sodium tert-butoxide (24.5 g, 6.4 mmol) was deaerated and heated under an argon (Ar) atmosphere at about 80° C. for about 4 hours. After cooling in the air, the reaction solution was filtered using Florisil®, and the residue obtained by concentration was separated by column chromatography to obtain Compound 1 (26.5 g, 45.3 mmol, 71%). The molecular weight of Compound 1 measured by Fast Atom Bombardment Mass Spectrometry (FAB-MS) was 583.

2. Synthesis of Compound 4

Synthesis of Intermediate E

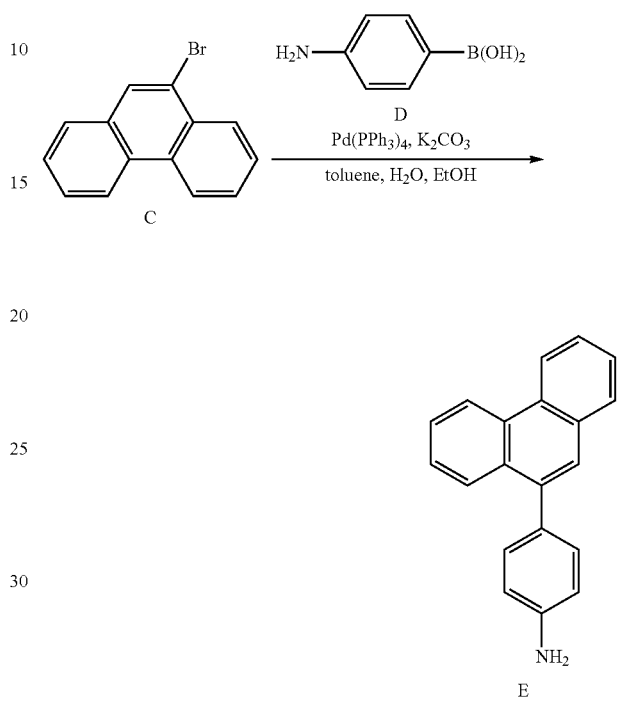

A toluene/EtOH/H$_2$O suspension (1200/120/240 ml) of Compound C (37.6 g, 146.1 mmol), Compound D (20.0 g, 146.1 mmol), tetrakis(triphenylphosphine)palladium(0) (8.4 g, 7.3 mmol), and potassium carbonate (24.2 g, 175.3 mmol) was deaerated and heated under an argon (Ar) atmosphere at about 80° C. for about 4 hours. After cooling in the air, the reaction solution was filtered using Florisil, and the residue obtained by concentration was separated by column chromatography to obtain Intermediate E (25.5 g, 94.9 mmol, 65%). The molecular weight of Intermediate E measured by FAB-MS was 269.

Synthesis of Compound 4

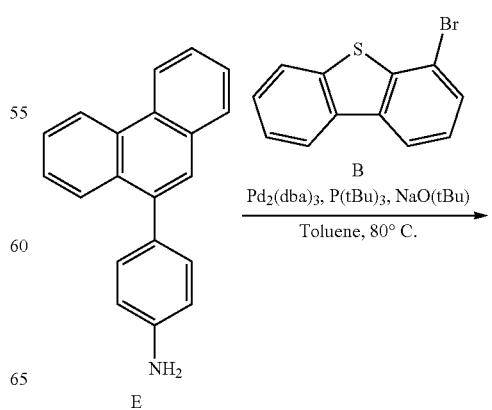

-continued

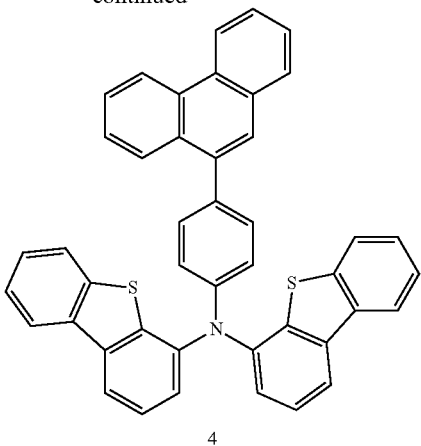

4

A toluene suspension (940 ml) of Intermediate E (14.0 g, 52.0 mmol), Compound B (27.4 g, 104.0 mmol), tris(dibenzylideneacetone)dipalladium(0) (4.8 g, 5.2 mmol), tri-tert-butylphosphine (1.7 g, 8.3 mmol), and sodium tert-butoxide (20.0 g, 5.2 mmol) was deaerated and heated under an argon (Ar) atmosphere at about 80° C. for about 4 hours. After cooling in the air, the reaction solution was filtered using Florisil, and the residue obtained by concentration was separated by column chromatography to obtain Compound 4 (22.4 g, 35.4 mmol, 68%). The molecular weight of Compound 4 measured by FAB-MS was 633.

3. Synthesis of Compound 12
Synthesis of Intermediate H

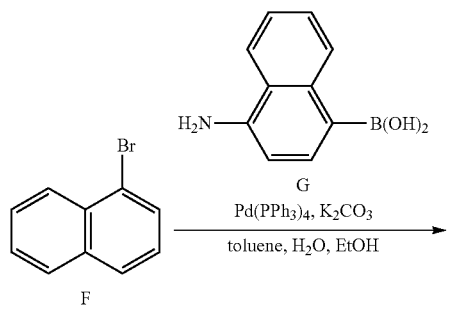

A toluene/EtOH/H₂O suspension (880/90/180 ml) of Compound F (22.1 g, 107.0 mmol), Compound G (20.0 g, 187.0 mmol), tetrakis(triphenylphosphine)palladium(0) (6.2 g, 5.35 mmol), and potassium carbonate (17.7 g, 128.3 mmol) was deaerated and heated under an argon (Ar) atmosphere at about 80° C. for about 4 hours. After cooling in the air, the reaction solution was filtered using Florisil, and the residue obtained by concentration was separated by column chromatography to obtain Intermediate H (15.8 g, 58.8 mmol, 55%). The molecular weight of Intermediate H measured by FAB-MS was 269.

Synthesis of Compound 12

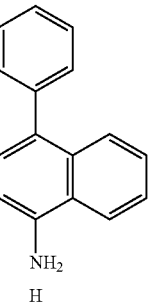
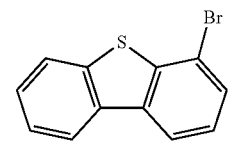

H

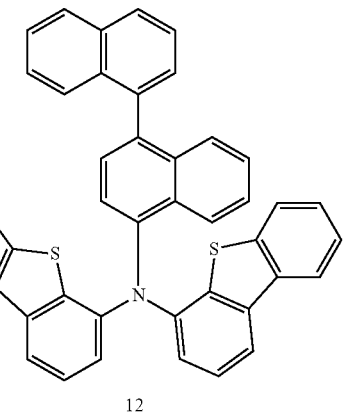

12

A toluene suspension (940 ml) of Intermediate H (14.0 g, 52.0 mmol), Compound B (27.4 g, 104.0 mmol), tris(dibenzylideneacetone)dipalladium(0) (4.8 g, 5.2 mmol), tri-tert-butylphosphine (1.7 g, 8.3 mmol), and sodium tert-butoxide (20.0 g, 5.2 mmol) was deaerated and heated under an argon (Ar) atmosphere at about 80° C. for about 4 hours. After cooling in the air, the reaction solution was filtered using Florisil, and the residue obtained by concentration was separated by column chromatography to obtain Compound 12 (24.7 g, 39.0 mmol, 75%). The molecular weight of Compound 12 measured by FAB-MS was 633.

4. Synthesis of Compound 27
Synthesis of Intermediate I

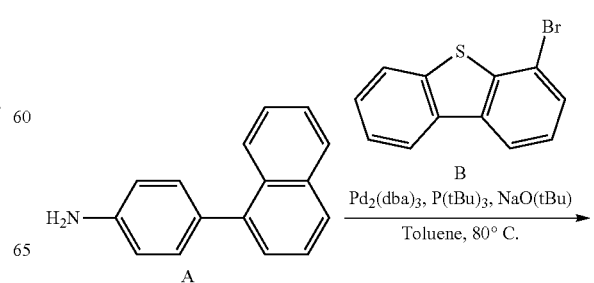

A

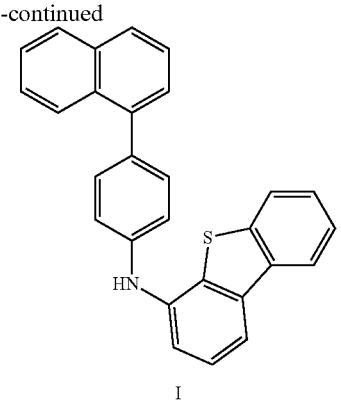

A toluene suspension (1600 ml) of Compound A (20.0 g, 91.2 mmol), Compound B (24.0 g, 91.2 mmol), tris(dibenzylideneacetone)dipalladium(0) (8.4 g, 9.1 mmol), tri-tert-butylphosphine (3.0 g, 14.6 mmol), and sodium tert-butoxide (17.5 g, 182.4 mmol) was deaerated and heated under an argon (Ar) atmosphere at about 80° C. for about 4 hours. After cooling in the air, the reaction solution was filtered using Florisil, and the residue obtained by concentration was separated by column chromatography to obtain Intermediate I (28.9 g, 72.1 mmol, 79%).

Synthesis of Compound 27

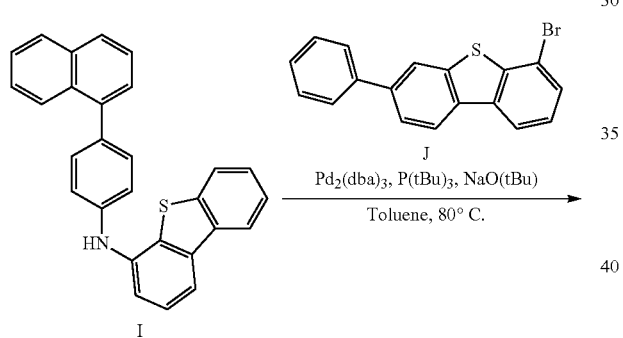

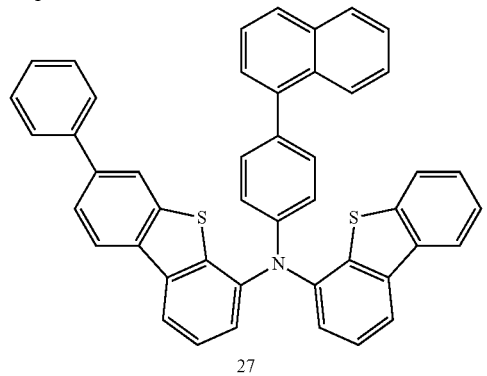

A toluene suspension (1100 ml) of Intermediate I (25.0 g, 62.3 mmol), Compound J (21.1 g, 62.3 mmol), tris(dibenzylideneacetone)dipalladium(0) (5.7 g, 6.2 mmol), tri(tert-butylphosphine) (2.0 g, 10.0 mmol), and sodium tert-butoxide (12.0 g, 124.5 mmol) was deaerated and heated under an argon (Ar) atmosphere at about 80° C. for about 4 hours. After cooling in the air, the reaction solution was filtered using Florisil, and the residue obtained by concentration was separated by column chromatography to obtain Compound 27 (29.6 g, 44.8 mmol, 72%). The molecular weight of the compound measured by FAB-MS was 659. Through the results, the compound thus synthesized was identified as Compound 27.

5. Synthesis of Compound 38

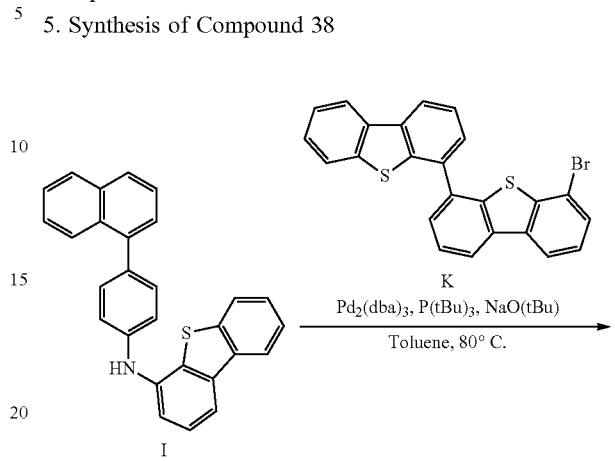

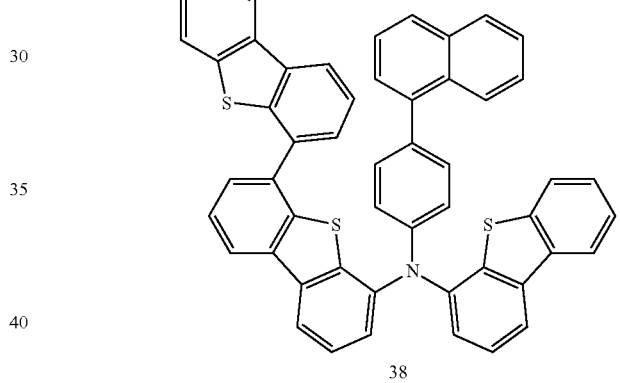

A toluene suspension (900 ml) of Compound I (20.0 g, 49.8 mmol), Compound K (22.2 g, 49.8 mmol), tris(dibenzylideneacetone)dipalladium(0) (4.6 g, 5.0 mmol), tri-tert-butylphosphine (1.6 g, 8.0 mmol), and sodium tert-butoxide (9.6 g, 99.6 mmol) was deaerated and heated under an argon (Ar) atmosphere at about 80° C. for about 4 hours. After cooling in the air, the reaction solution was filtered using Florisil, and the residue obtained by concentration was separated by column chromatography to obtain Compound 38 (25.9 g, 33.9 mmol, 68%). The molecular weight of the compound measured by FAB-MS was 765. Through the results, the compound thus synthesized was identified as Compound 38.

Experimental Examples

Device Manufacturing Examples

Organic electroluminescence devices of Examples 1 to 5 were manufactured using Compounds 1, 4, 12, 27 and 38 as hole transport materials.

Example Compounds
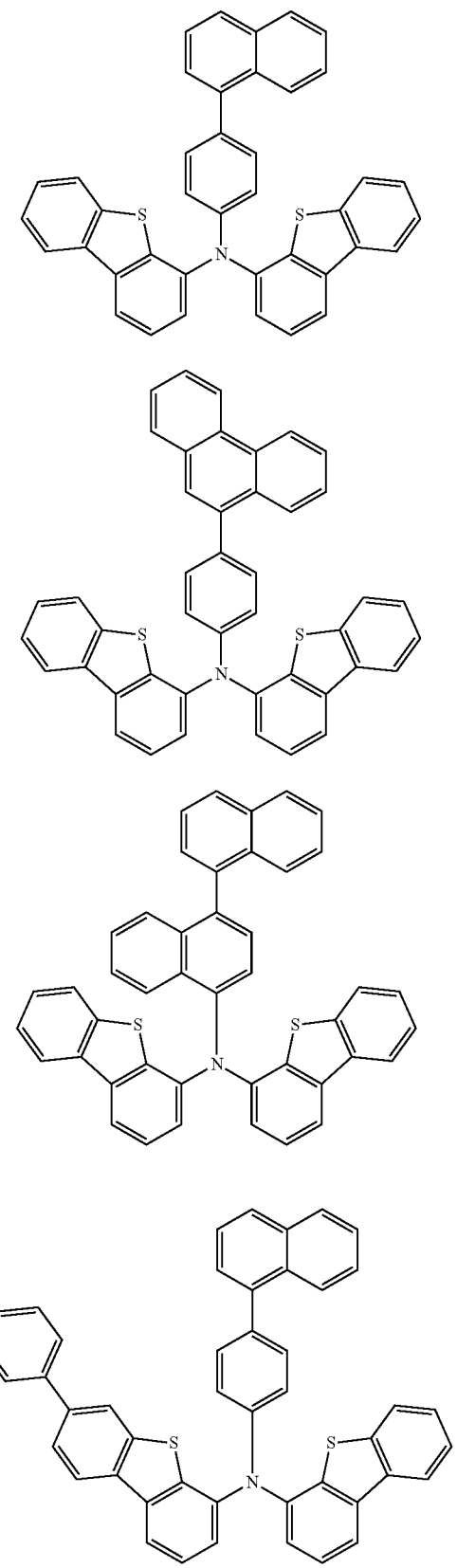
1
4
12
27
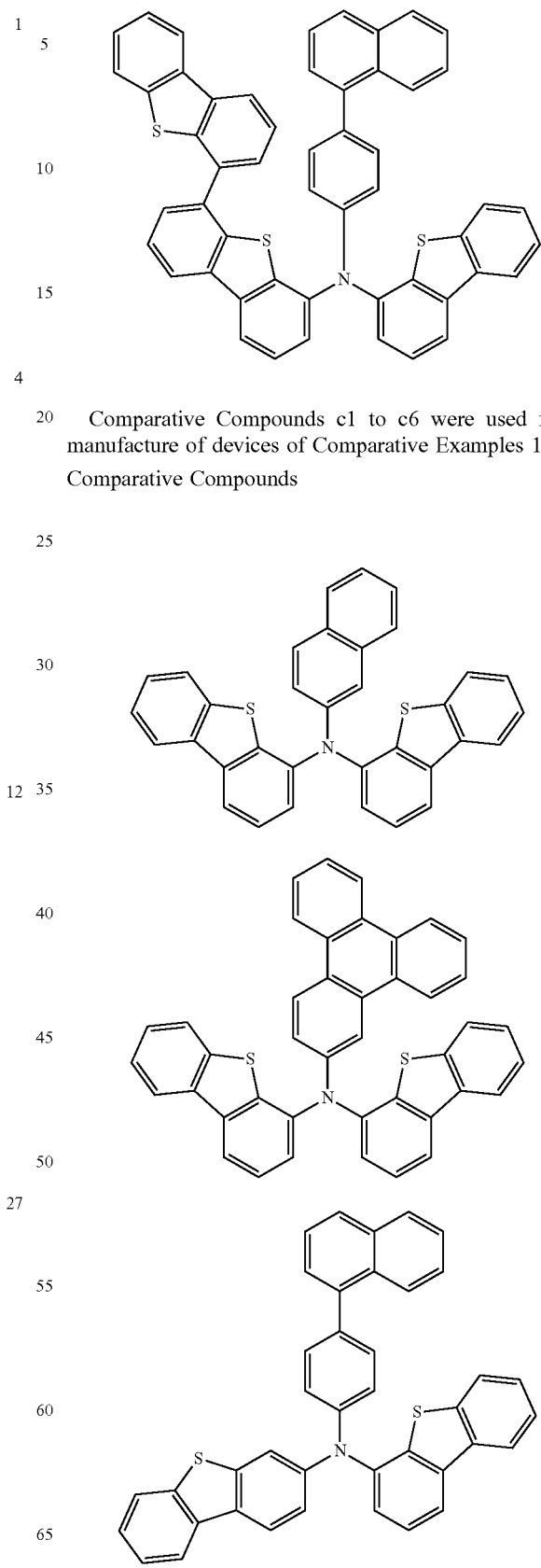
38
Comparative Compounds c1 to c6 were used for the manufacture of devices of Comparative Examples 1 to 6.
Comparative Compounds
c1
c2
c3

-continued

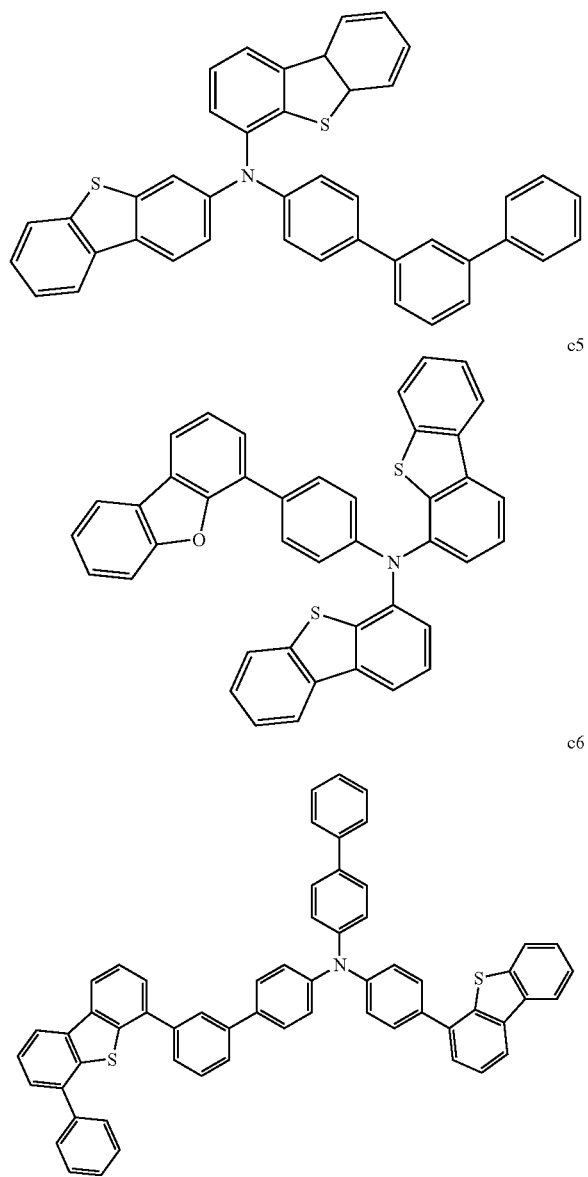

Organic electroluminescence devices of Examples 1 to 5 and Comparative Examples 1 to 6 were manufactured by forming a first electrode using ITO to a thickness of about 150 nm, a hole injection layer using 4,4',4"-tris{N-(1-naphthyl)-N-phenylamino}-triphenylamine (1-TNATA) to a thickness of about 60 nm, a hole transport layer using the respective one of the example compounds or the comparative compounds to a thickness of about 30 nm, an emission layer using dinaphthylanthracene (ADN) doped with 3% of 2,5,8,11-tetra-tert-butylperylene (TBP) to a thickness of about 25 nm, an electron transport layer using Alq$_3$ to a thickness of about 25 nm, an electron injection layer using LiF to a thickness of about 1 nm, and a second electrode using Al to a thickness of about 100 nm. Each layer was formed by a deposition method under vacuum.

Experimental Examples

The emission efficiency and emission life of the organic electroluminescence devices manufactured using Example Compounds 1, 4, 12, 27, and 38 and Comparative Compounds c1 to c6 were evaluated. The evaluation results are shown in Table 1 below. The evaluation results of the properties of the examples and the comparative examples in Table 1 are relative ratios of emission efficiency and emission life with respect to 100% of the emission efficiency and emission life of the organic electroluminescence device of Comparative Example 1, respectively.

TABLE 1

| Device manufacturing example | Hole transport layer compound | Emission efficiency (ratio relative to Comparative Example 1) | Emission life (ratio relative to Comparative Example 1) |
| --- | --- | --- | --- |
| Example 1 | Example Compound 1 | 110 | 130 |
| Example 2 | Example Compound 4 | 120 | 120 |
| Example 3 | Example Compound 12 | 125 | 105 |
| Example 4 | Example Compound 27 | 105 | 135 |
| Example 5 | Example Compound 38 | 120 | 100 |
| Comparative Example 1 | Comparative Compound c1 | 100 | 100 |
| Comparative Example 2 | Comparative Compound c2 | 30 | 105 |
| Comparative Example 3 | Comparative Compound c3 | 80 | 95 |
| Comparative Example 4 | Comparative Compound c4 | 80 | 90 |
| Comparative Example 5 | Comparative Compound c5 | 100 | 80 |
| Comparative Example 6 | Comparative Compound c6 | 70 | 100 |

Referring to the results of Table 1, Example 1 to Example 5 were found to show improved emission efficiency and/or device life when compared to Comparative Example 1 to Comparative Example 6. More particularly, Example 1 to Example 5 were found to show improved emission efficiency and/or device life when compared to Comparative Example 1 to Comparative Example 5, which included hole transport materials having similar core structures.

The example compounds included in Example 1 to Example 5 include two dibenzothiophene groups which are bonded to an amine core at each carbon position number of 4 (as shown in the image of the compounds), according to embodiments of the present disclosure. Since the compound of the present embodiments has high amorphous properties, if the compound is used as a hole transport material, high hole transport properties may be attained, and high emission efficiency and long life of an organic electroluminescence device may be secured. In addition, a divalent phenyl group or a naphthyl group, which is bonded to an amine core (e.g., to the central N atom), is protected by an aryl substituent having 10 or more carbon atoms, and the decomposition of the amine compound during the driving of a device may be restrained (reduced), emission efficiency may be maintained high, and the life of the device may increase.

Comparative Compound c1, which was included in Comparative Example 1, includes two dibenzothiophene groups which are bonded to an amine core at each carbon number of 4 (e.g., at the same positions as in the compound of Formula 1), but no substituent for the naphthyl group which is bonded to the amine core is present.

Accordingly, effect of protecting the naphthyl group is not achieved when compared to the example compounds, and the amine compound may be decomposed during the driving of a device. Thus, the emission efficiency and the device life of Comparative Example 1 may decrease when compared to the examples.

Comparative Compound c2, which is included in Comparative Example 2, includes two dibenzothiophene groups which are bonded to an amine core at each carbon position number of 4, but a triphenylene group is connected to the amine core. The triphenylene group lowers the LUMO of the amine compound, and the hole transport properties of Comparative Compound c2 are decreased when compared to the example compounds, and the emission efficiency and the device life of Comparative Example 2 may decrease when compared to the examples.

In Comparative Compounds c3 and c4, which are respectively included in Comparative Examples 3 and 4, dibenzothiophene groups are bonded to an amine core, but one dibenzothiophene group is bonded to the amine group not at the carbon position number of 4 but at the carbon position number of 3. If the dibenzothiophene group is combined with the amine core at the carbon position number of 3 (as shown in Comparative Compounds c3 and c4), the crystallinity of the amine compound may increase, and amorphous properties may be reduced when compared to the example compounds. Accordingly, the hole transport properties of Comparative Compounds c3 and c4 decrease when compared to the example compounds, and the emission efficiency and the device life of Comparative Examples 3 and 4 decrease when compared to the examples.

Comparative Compound c5 included in Comparative Example 5 includes two dibenzothiophene groups which are combined with an amine core at the carbon position number of 4, and a substituted phenylene group on the amine core. Here, a dibenzofuran group is connected to the phenylene group in Comparative Compound c5, and the stability of the compound is reduced and is liable (e.g., more prone) to decompose when compared to the example compounds. Accordingly, the emission efficiency and the device life of Comparative Example 5 decrease when compared to the examples.

Comparative Compound c6 included in Comparative Example 6 includes two dibenzothiophene groups which are bonded to an amine core at each carbon position number of 4, but instead of being directly bonded to the amine core, the dibenzothiophene groups are bonded via a phenylene group or a divalent biphenyl group. Accordingly, the distance between the debenzothiophene groups and the amine core increases, and the hole transport properties of Comparative Compound c6 were reduced when compared to the example compounds. Thus, the emission efficiency and the device life of Comparative Example 6 were reduced when compared to the examples.

The organic electroluminescence device according to an embodiment of the present disclosure has excellent emission efficiency and long life.

The amine compound according to an embodiment of the present disclosure may be used as a material for an organic electroluminescence device.

An organic electroluminescence device including the amine compound according to an embodiment of the present disclosure may achieve excellent emission efficiency and long life.

Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present invention have been described herein, it will be understood that the present invention should not be limited to these example embodiments but various changes and modifications can be made by one ordinary skilled in the art within the spirit and scope of the present invention as defined by the following claims and equivalents thereof.

What is claimed is:
1. An organic electroluminescence device, comprising:
a first electrode;
a hole transport region on the first electrode;
an emission layer on the hole transport region;
an electron transport region on the emission layer; and
a second electrode on the electron transport region,
wherein the hole transport region comprises an amine compound represented by the following Formula 1:

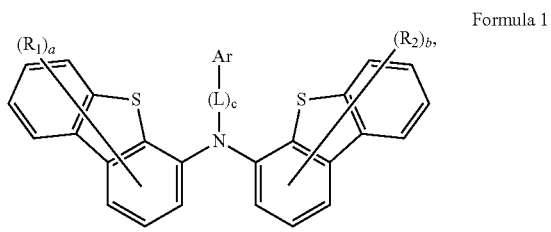

Formula 1 wherein in Formula 1,
Ar is a substituted or unsubstituted naphthyl group, a substituted or unsubstituted phenanthryl group, or a substituted or unsubstituted aryl group having 16 to 60 carbon atoms for forming a ring,
L is a substituted or unsubstituted arylene group having 6 to 30 carbon atoms for forming a ring,
$R_1$ and $R_2$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, "a" and "b" are each independently an integer of 0 to 7, and "c" is an integer of 1 to 4.

2. The organic electroluminescence device of claim 1, wherein the hole transport region comprises:
a hole injection layer on the first electrode; and
a hole transport layer on the hole injection layer,
wherein the hole transport layer comprises the amine compound represented by Formula 1.

3. The organic electroluminescence device of claim 1, wherein the hole transport region comprises a plurality of layers, and
a layer in contact with the emission layer among the plurality of the layers comprises the amine compound represented by Formula 1.

4. The organic electroluminescence device of claim 1, wherein L is a substituted or unsubstituted phenylene group, or a substituted or unsubstituted naphthylene group.

5. The organic electroluminescence device of claim 1, wherein the amine compound represented by Formula 1 is represented by one of the following Formulae 2-1 to 2-3:

Formula 2-1

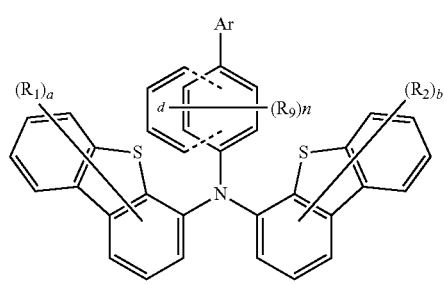

Formula 2-2

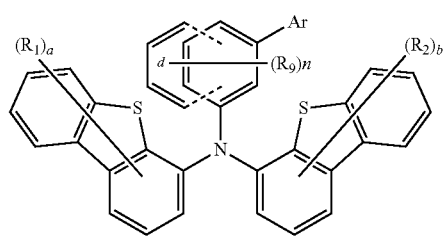

Formula 2-3

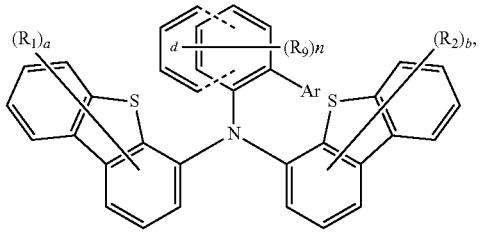

wherein in Formulae 2-1 to 2-3,

"d" is 0 or 1, $R_9$ is hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, "n" is an integer of 0 to 6, and Ar, $R_1$, $R_2$, "a" and "b" are the same as defined in Formula 1.

6. The organic electroluminescence device of claim 5, wherein the amine compound represented by one of Formulae 2-1 to 2-3 is represented by one of the following Formulae 2-1-1 to 2-3-2:

Formula 2-1-1

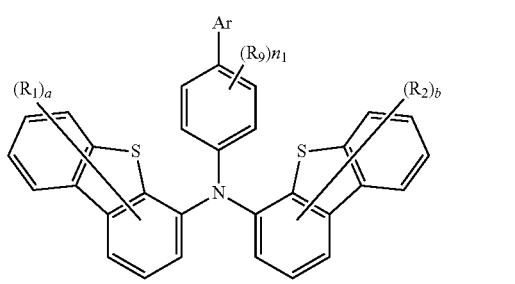

Formula 2-1-2

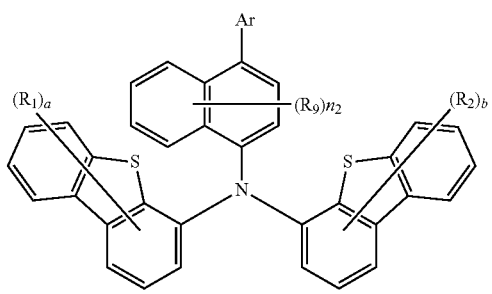

Formula 2-2-1

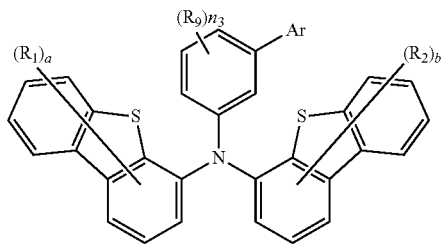

Formula 2-2-2

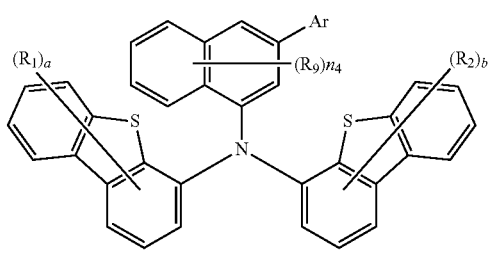

Formula 2-3-1

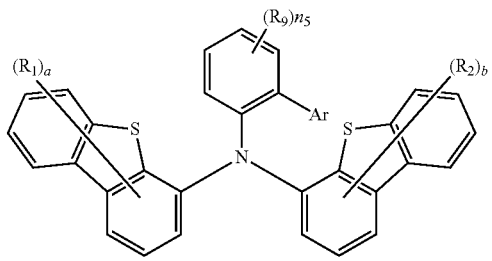

-continued

Formula 2-3-2

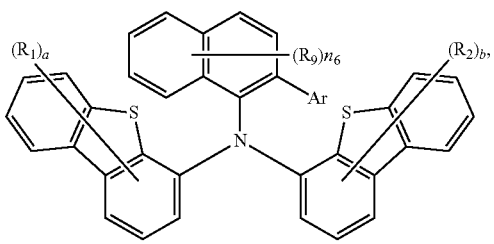

wherein in Formulae 2-1-1 to 2-3-2, n1, n3 and n5 are each independently an integer of 0 to 4, n2, n4 and n6 are each independently an integer of 0 to 6, $R_9$ is the same as defined in Formulae 2-1 to 2-3, and Ar, $R_1$, $R_2$, "a" and "b" are the same as defined in Formula 1.

7. The organic electroluminescence device of claim 1, wherein Ar is the substituted or unsubstituted naphthyl group, or the substituted or unsubstituted phenanthryl group.

8. The organic electroluminescence device of claim 1, wherein the amine compound represented by Formula 1 is represented by one of the following Formulae 3-1 to 3-3:

Formula 3-1

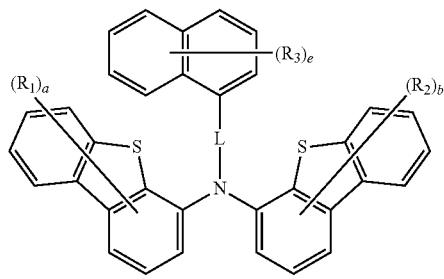

Formula 3-2

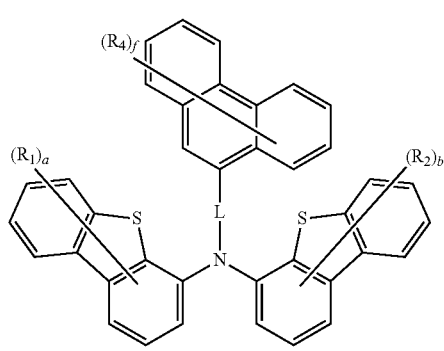

Formula 3-3 wherein in Formulae 3-1 to 3-3, $R_3$ to $R_5$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, "e" is an integer of 0 to 7, "f" and "g" are each independently an integer of 0 to 9, and $R_1$, $R_2$, "a", "b", and L are the same as defined in Formula 1.

9. The organic electroluminescence device of claim 1, wherein at least one of "a" or "b" is 1 or 2, and $R_1$ and $R_2$ are each independently deuterium, a halogen atom, a substituted or unsubstituted alkyl group having 1 to 10 carbon atoms, a substituted or unsubstituted phenyl group, a substituted or unsubstituted naphthyl group, a substituted or unsubstituted phenanthryl group, a substituted or unsubstituted carbazolyl group, a substituted or unsubstituted dibenzofuranyl group, or a substituted or unsubstituted dibenzothiophenyl group.

10. The organic electroluminescence device of claim 1, wherein the amine compound represented by Formula 1 is represented by the following Formula 4:

Formula 4

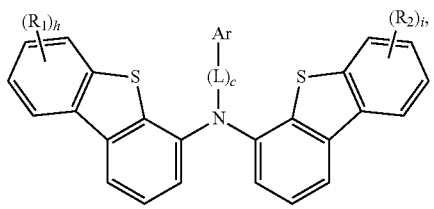

wherein in Formula 4,

"h" and "i" are an integer of 0 to 2, at least one of "h" or "i" is 1 or 2, $R_1$ and $R_2$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, Ar, L and "c" are the same as defined in Formula 1.

11. The organic electroluminescence device of claim 1, wherein the amine compound represented by Formula 1 is represented by the following Formula 5:

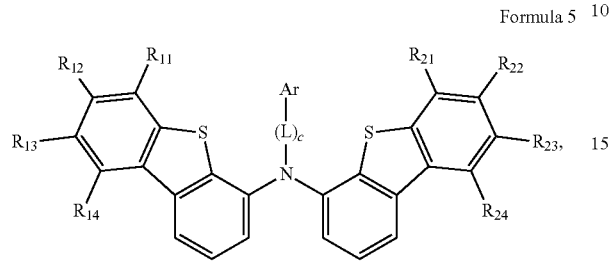

Formula 5 wherein in Formula 5, $R_{11}$ to $R_{14}$ and $R_{21}$ to $R_{24}$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, where at least one of $R_{11}$ to $R_{14}$ and $R_{21}$ to $R_{24}$ is deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, two members in at least one group selected from $R_{11}$ and $R_{21}$, $R_{12}$ and $R_{22}$, $R_{13}$ and $R_{23}$, and $R_{14}$ and $R_{24}$ are different from each other, and Ar, L and "c" are the same as defined in Formula 1.

12. The organic electroluminescence device of claim 1, wherein the amine compound represented by Formula 1 is at least one selected from compounds represented by the following Compound Group 1:

Compound Group 1

1

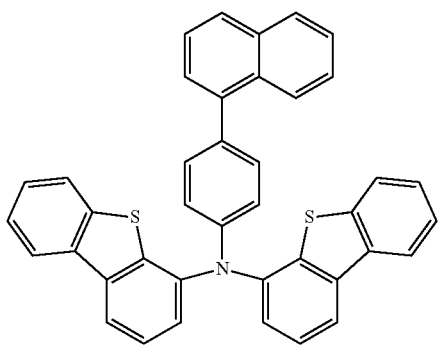

-continued

2

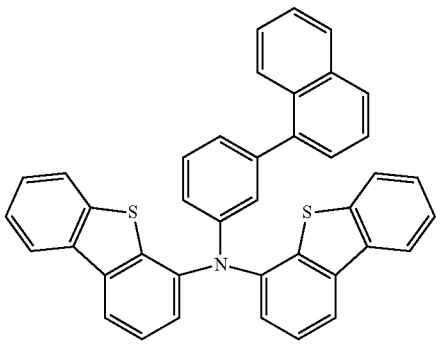

3

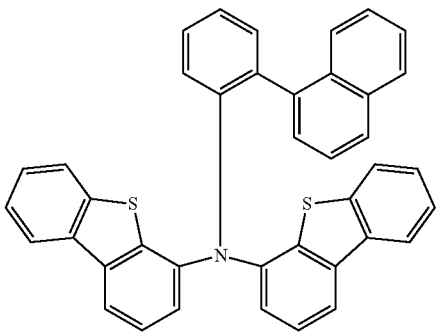

4

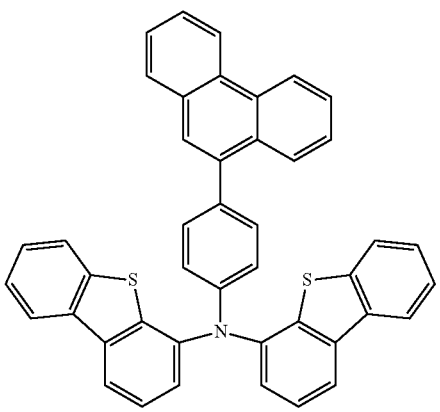

5

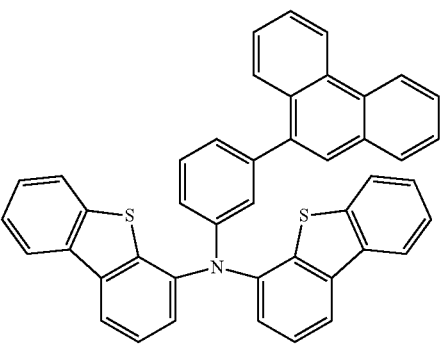

6
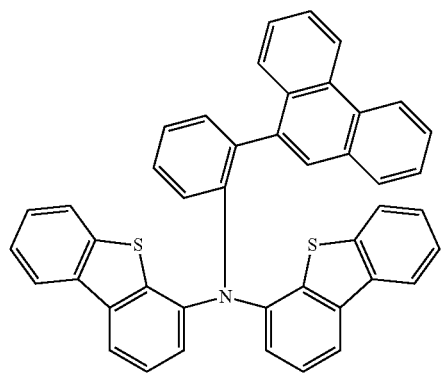
7
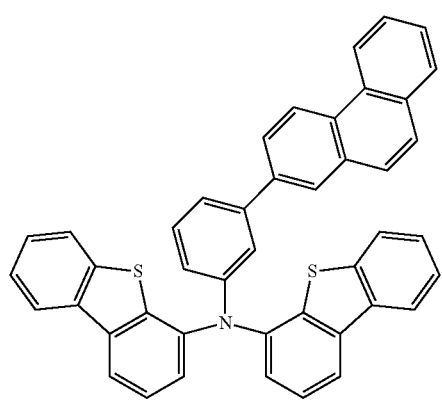
8
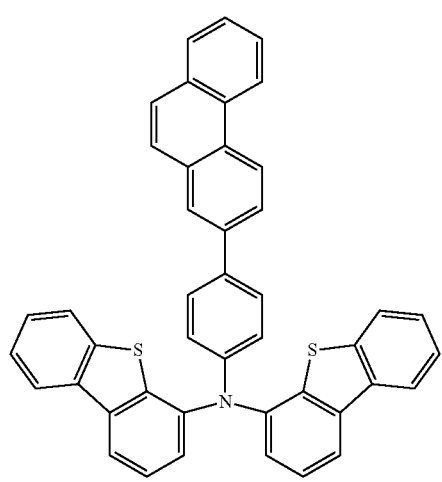
9
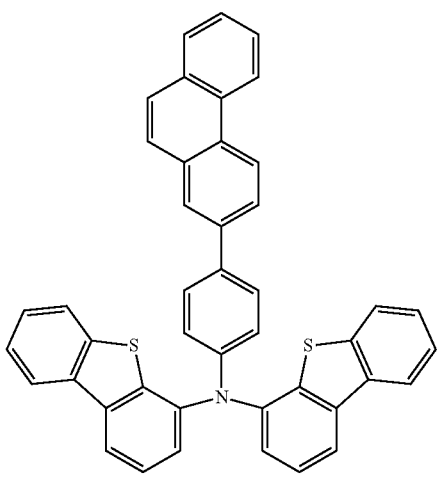
10
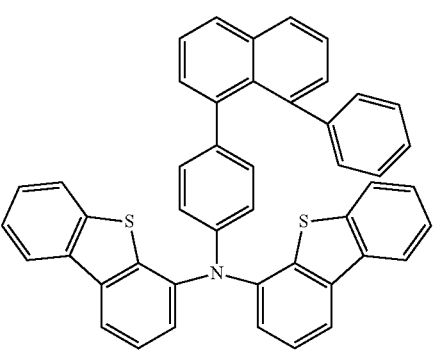
11
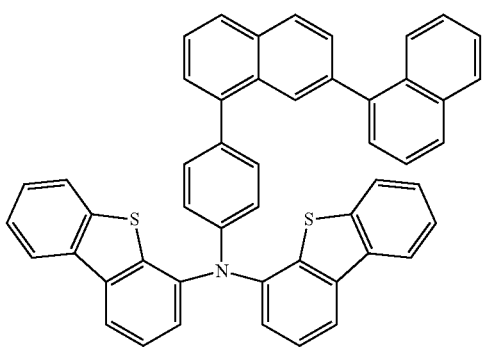
12
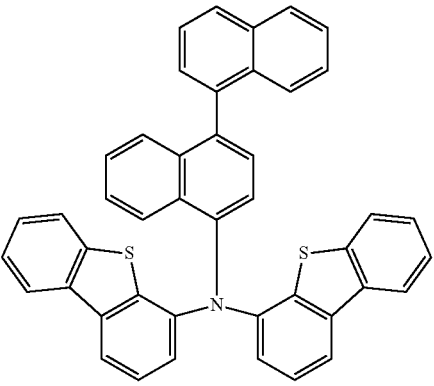

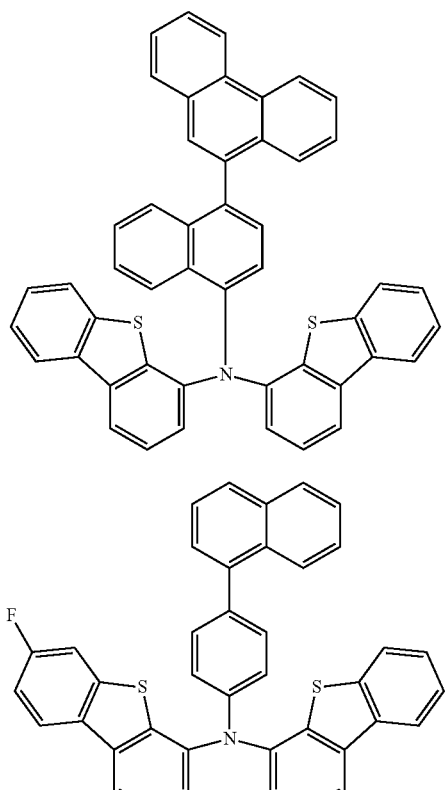
13
14
15
16
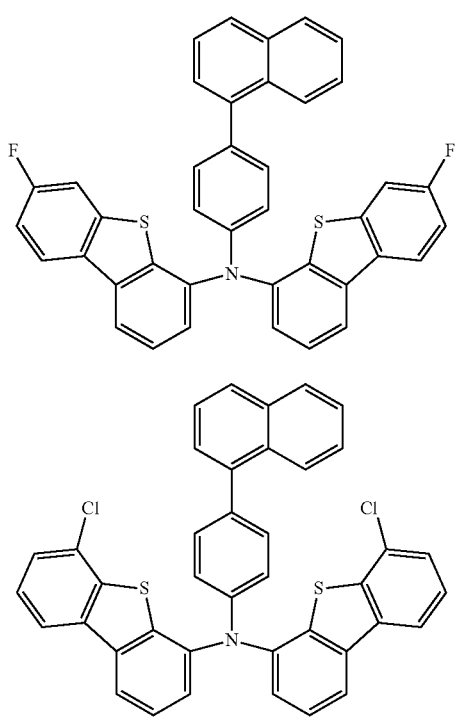
17
18
19
20

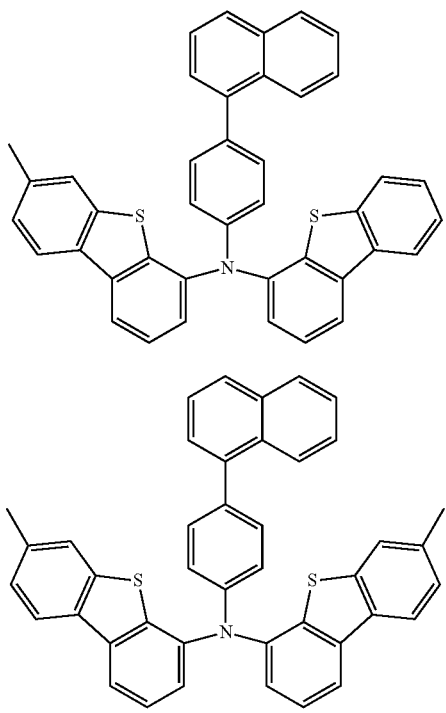
21
22
23
24
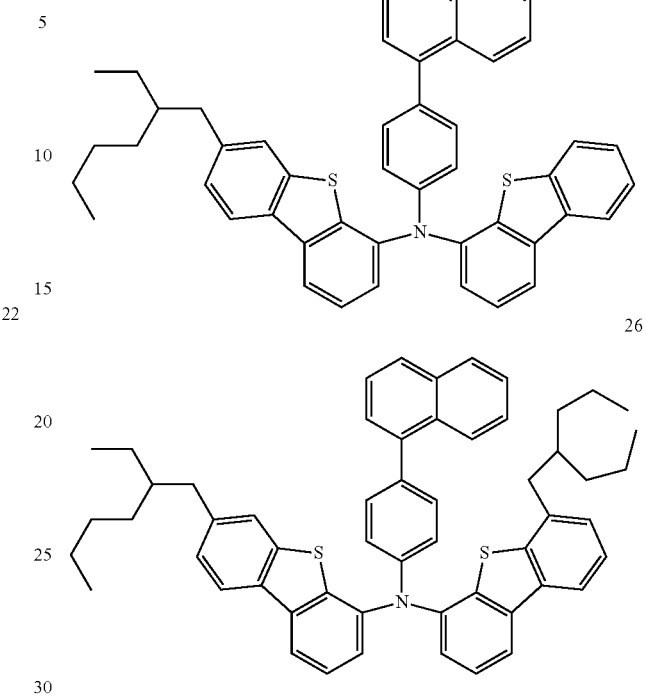
25
26
27
28

29
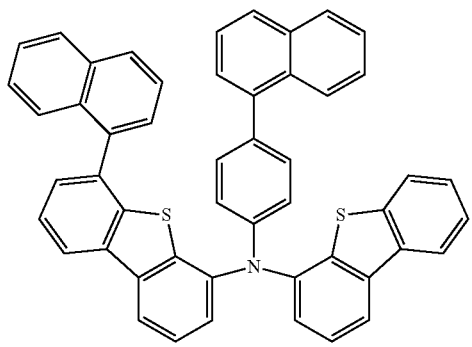
30
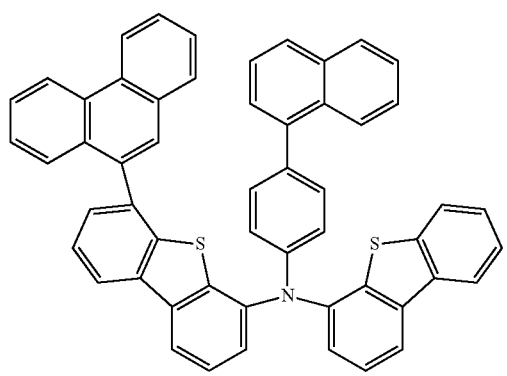
31
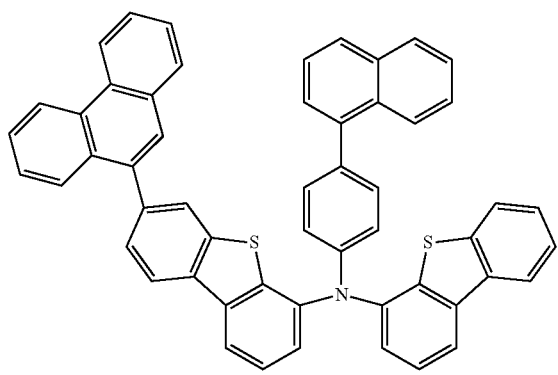
32
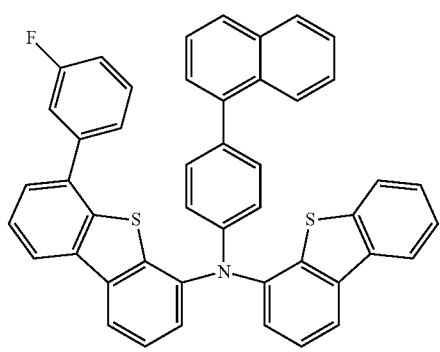
33
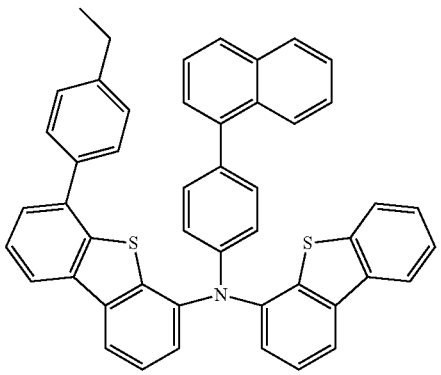
34
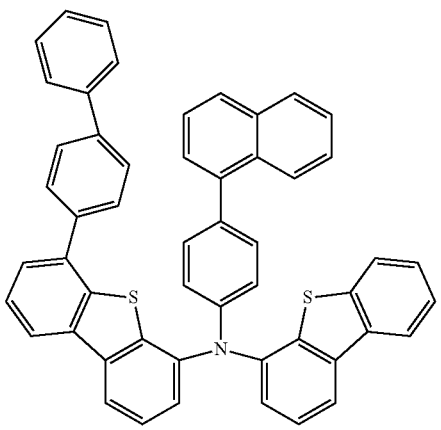
35
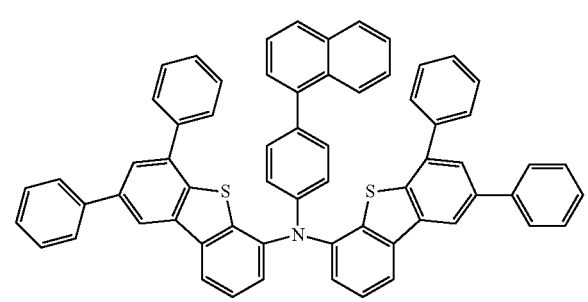
36
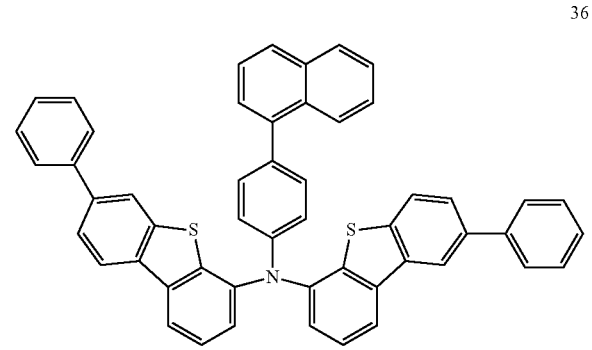

37
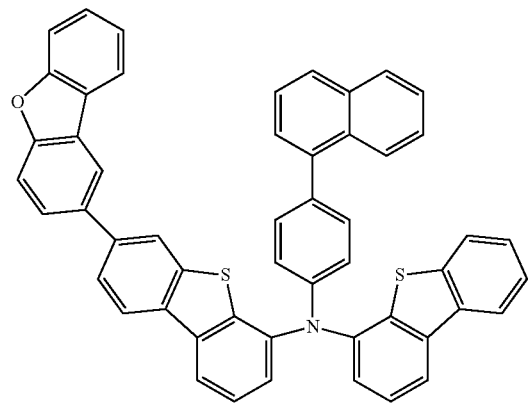
38
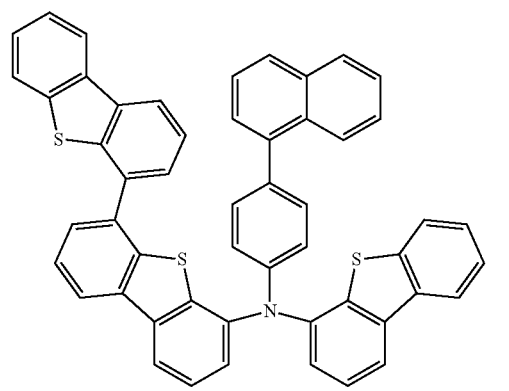
39
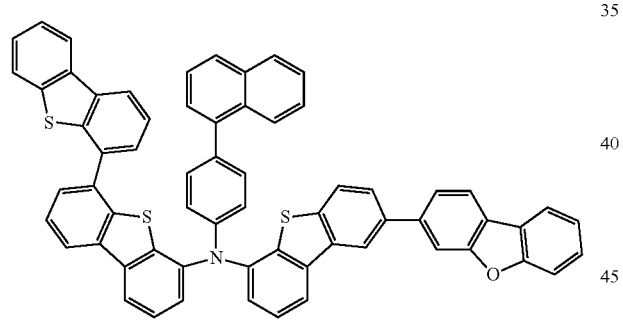
40
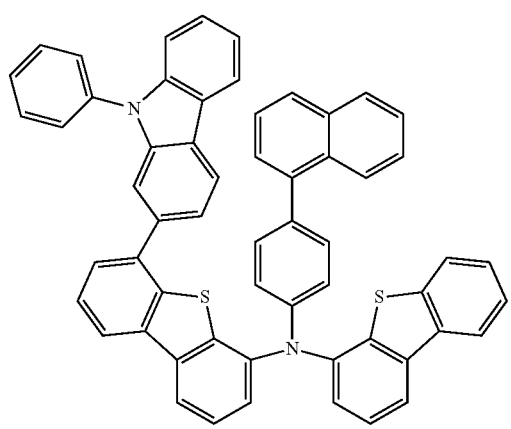
41
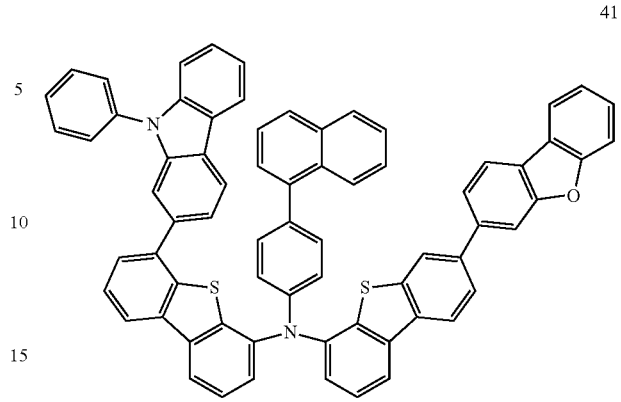
42
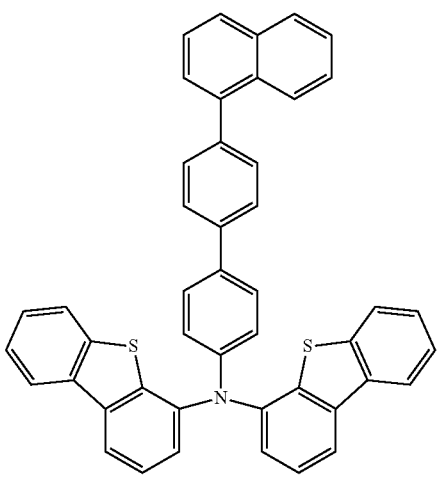
43
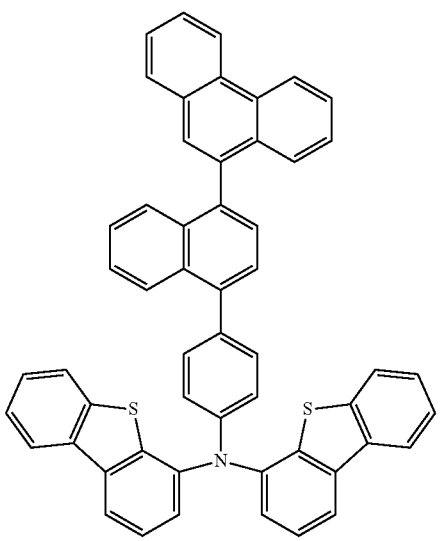

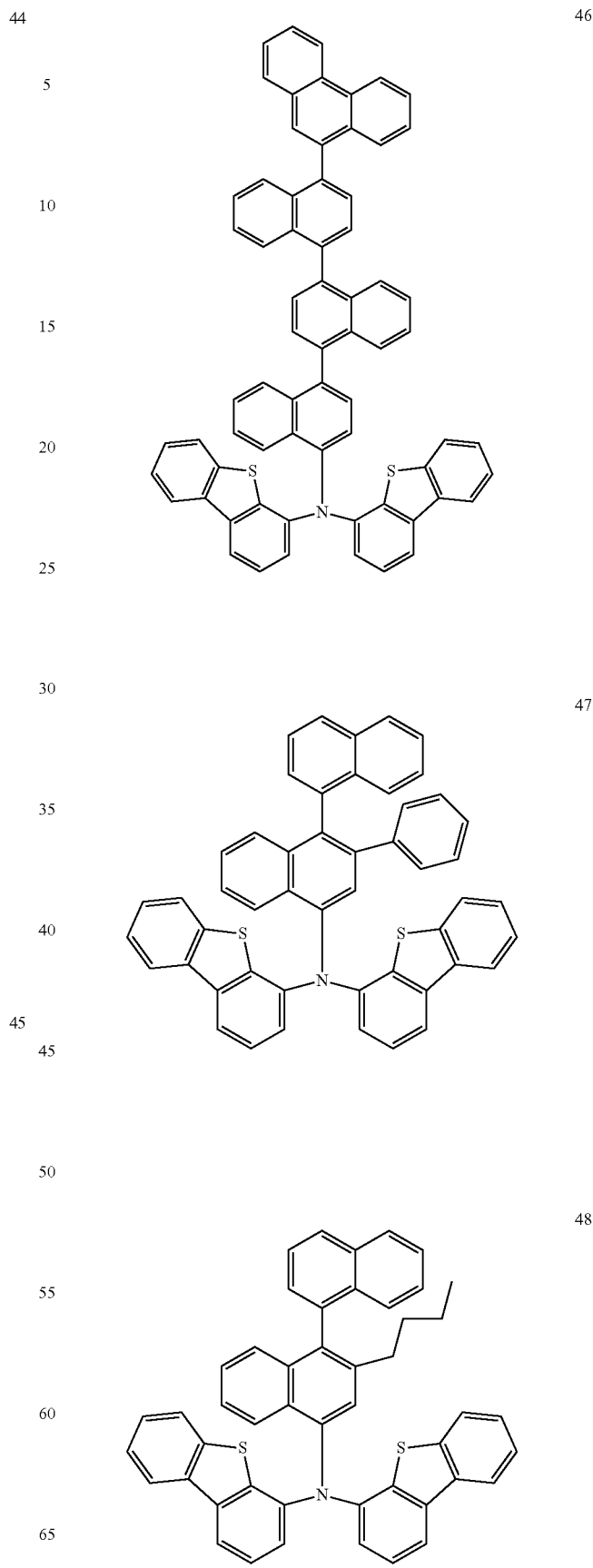

-continued

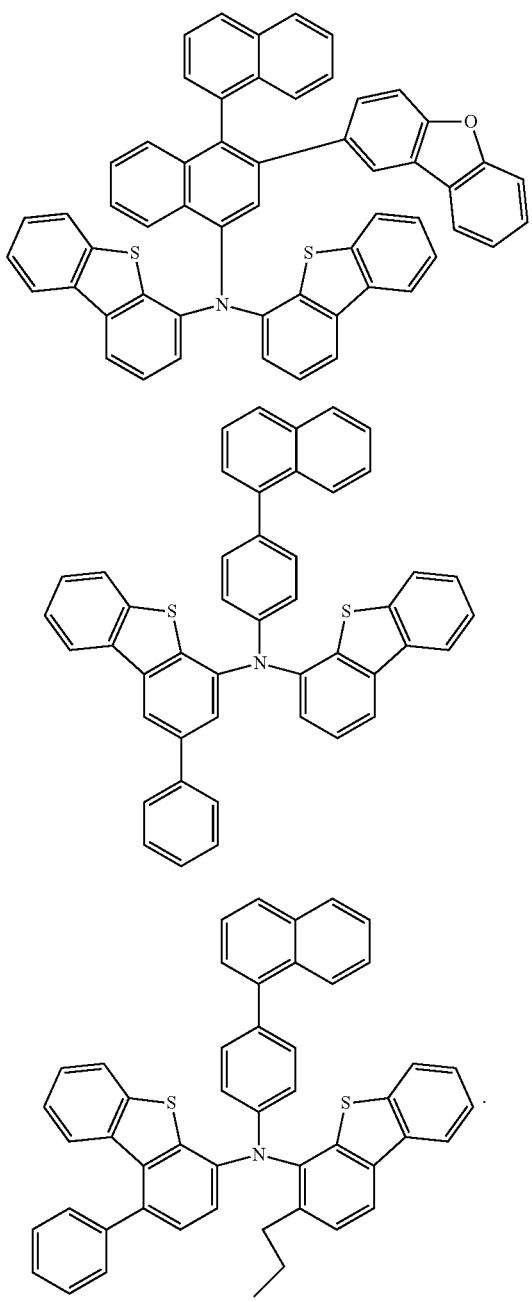

13. An amine compound represented by the following Formula 1:

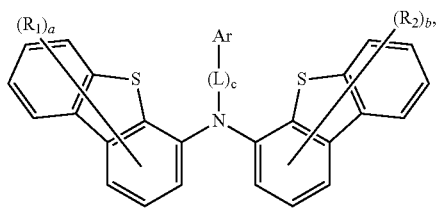

wherein in Formula 1,
Ar is a substituted or unsubstituted naphthyl group, a substituted or unsubstituted phenanthryl group, or a substituted or unsubstituted aryl group having 16 to 60 carbon atoms for forming a ring,
L is a substituted or unsubstituted arylene group having 6 to 30 carbon atoms for forming a ring,
$R_1$ and $R_2$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring,
"a" and "b" are each independently an integer of 0 to 7, and
"c" is an integer of 1 to 4.

14. The amine compound of claim 13, wherein L is a substituted or unsubstituted phenylene group, or a substituted or unsubstituted naphthylene group.

15. The amine compound of claim 13, wherein the amine compound represented by Formula 1 is represented by one of the following Formulae 2-1 to 2-3:

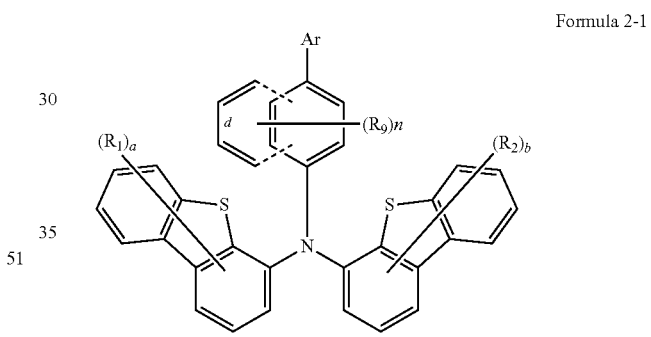

Formula 2-1

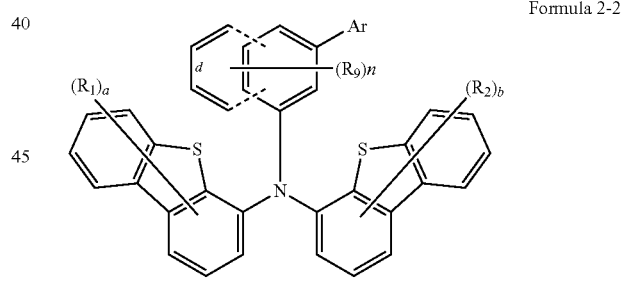

Formula 2-2

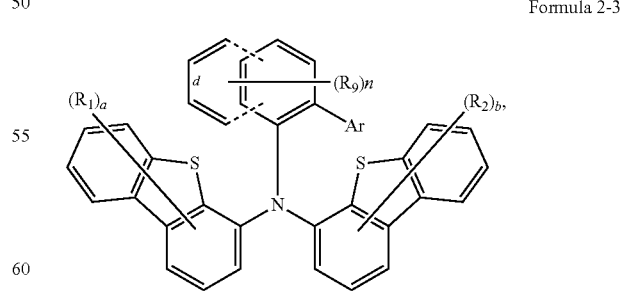

Formula 2-3 wherein in Formulae 2-1 to 2-3,
"d" is 0 or 1,
$R_9$ is hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms, "n" is an integer of 0 to 6, and Ar, $R_1$, $R_2$, "a" and "b" are the same as defined in Formula 1.

16. The amine compound of claim 15, wherein the amine compound represented by one of Formulae 2-1 to 2-3 is represented by one of the following Formulae 2-1-1 to 2-3-2:

Formula 2-1-1

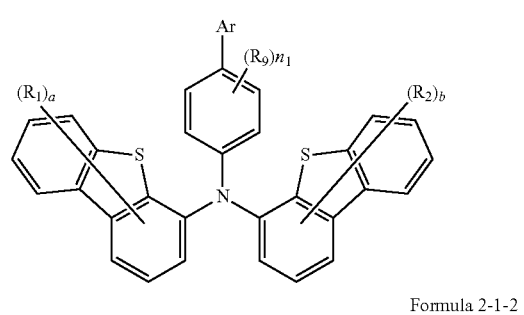

Formula 2-1-2

Formula 2-2-1

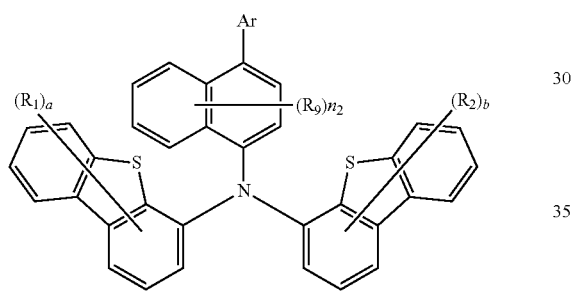

Formula 2-2-2

Formula 2-3-1

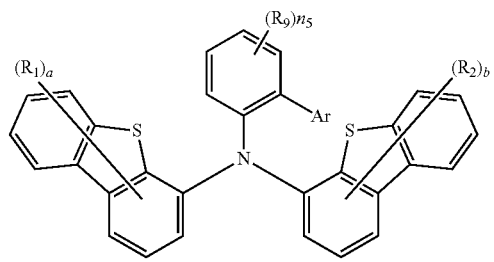

Formula 2-3-2

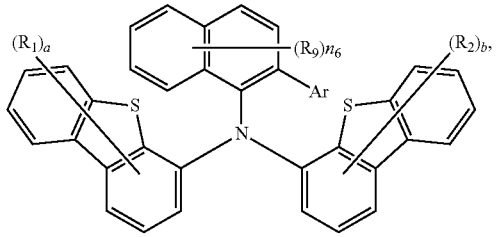

wherein in Formulae 2-1-1 to 2-3-2, n1, n3 and n5 are each independently an integer of 0 to 4, n2, n4 and n6 are each independently an integer of 0 to 6, $R_9$ is the same as defined in Formulae 2-1 to 2-3, and Ar, $R_1$, $R_2$, "a" and "b" are the same as defined in Formula 1.

17. The amine compound of claim 13, wherein Ar is the substituted or unsubstituted naphthyl group, or the substituted or unsubstituted phenanthryl group.

18. The amine compound of claim 13, wherein the amine compound represented by Formula 1 is represented by one of the following Formulae 3-1 to 3-3:

Formula 3-1

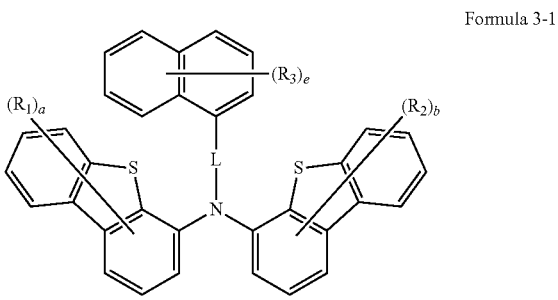

Formula 3-2

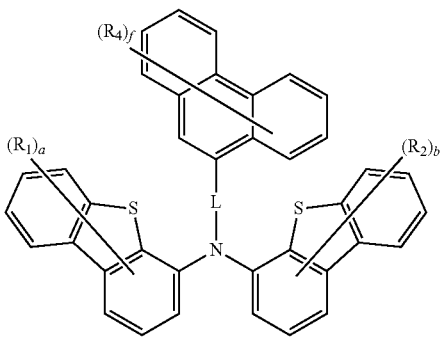

-continued

Formula 3-3

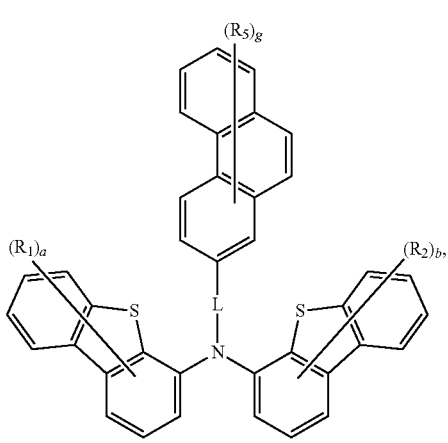

wherein in Formulae 3-1 to 3-3, $R_3$ to $R_5$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, "e" is an integer of 0 to 7, "f" and "g" are each independently an integer of 0 to 9, and $R_1$, $R_2$, "a", "b", and L are the same as defined in Formula 1.

19. The amine compound of claim 13, wherein at least one of "a" or "b" is 1 or 2, and $R_1$ and $R_2$ are each independently deuterium, a halogen atom, a substituted or unsubstituted alkyl group having 1 to 10 carbon atoms, a substituted or unsubstituted phenyl group, a substituted or unsubstituted naphthyl group, a substituted or unsubstituted phenanthryl group, a substituted or unsubstituted carbazolyl group, a substituted or unsubstituted dibenzofuranyl group, or a substituted or unsubstituted dibenzothiophenyl group.

20. The amine compound of claim 13, wherein the amine compound represented by Formula 1 is represented by the following Formula 4:

Formula 4

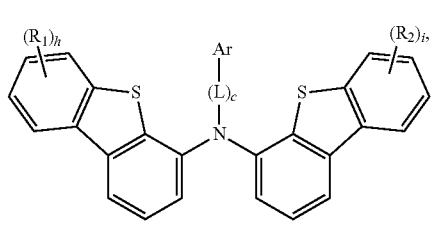

wherein in Formula 4,

"h" and "i" are an integer of 0 to 2, at least one of "h" and "i" is 1 or 2, $R_1$ and $R_2$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, Ar, L and "c" are the same as defined in Formula 1.

21. The amine compound of claim 13, wherein the amine compound represented by Formula 1 is represented by the following Formula 5:

Formula 5

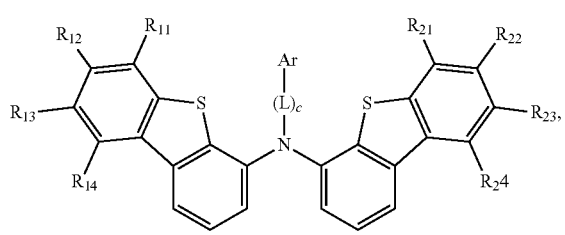

wherein in Formula 5, $R_{11}$ to $R_{14}$ and $R_{21}$ to $R_{24}$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, where at least one of $R_{11}$ to $R_{14}$ and $R_{21}$ to $R_{24}$ is deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, two members in at least one group selected from $R_{11}$ and $R_{21}$, $R_{12}$ and $R_{22}$, $R_{13}$ and $R_{23}$, and $R_{14}$ and $R_{24}$ are different from each other, and Ar, L and "c" are the same as defined in Formula 1.

22. The amine compound of claim 13, wherein the amine compound represented by Formula 1 is at least one selected from compounds represented by the following Compound Group 1:

Compound Group 1

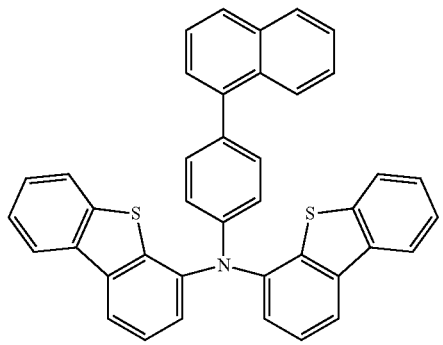

1

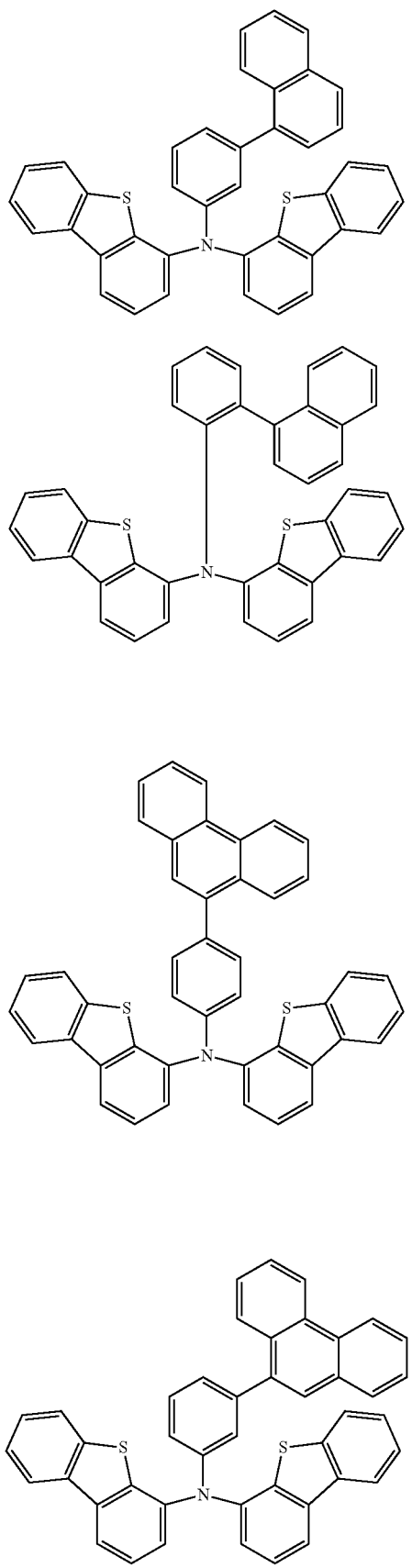
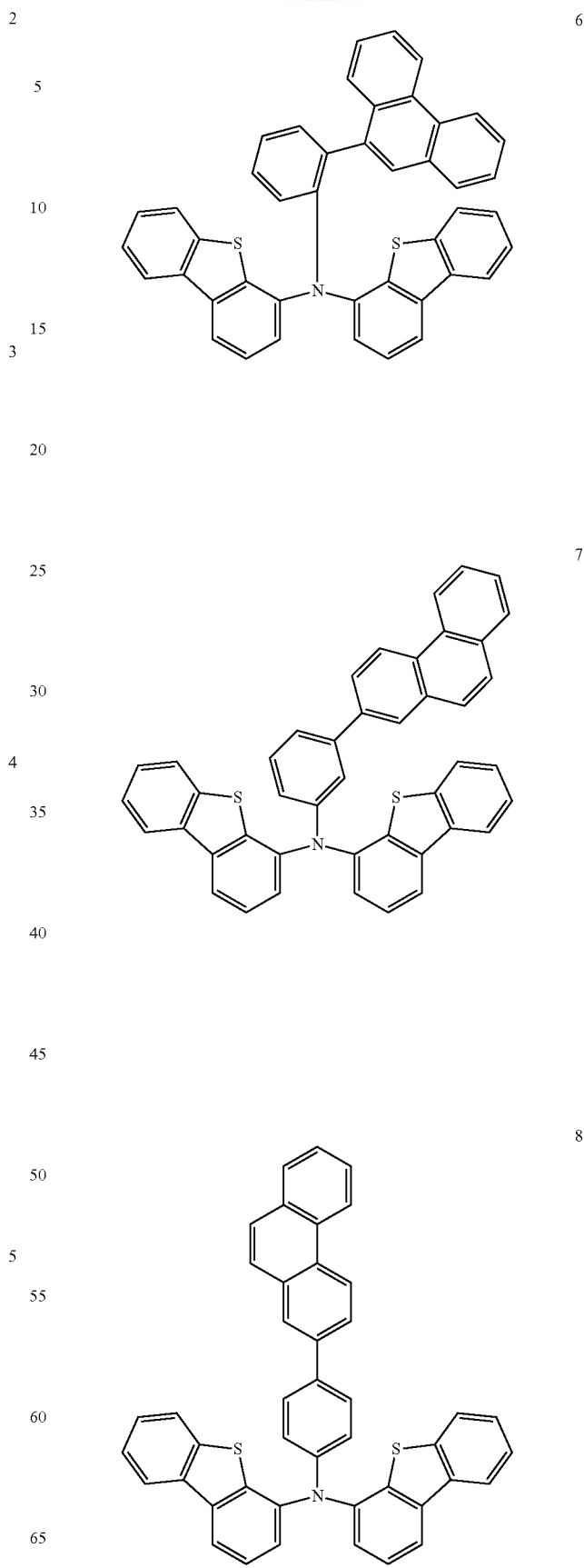

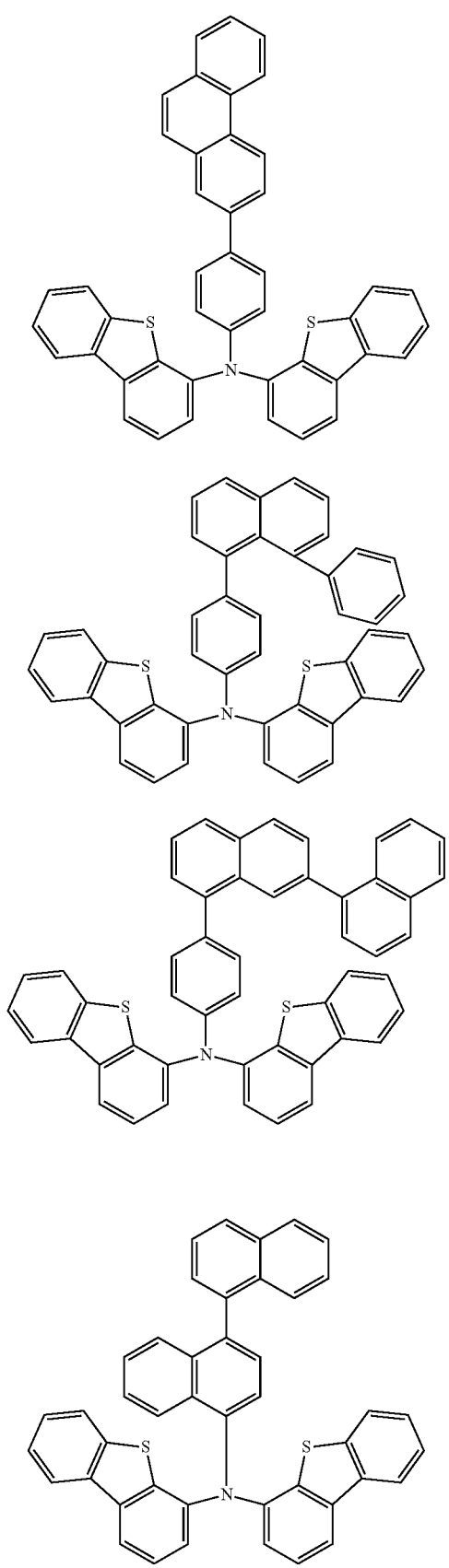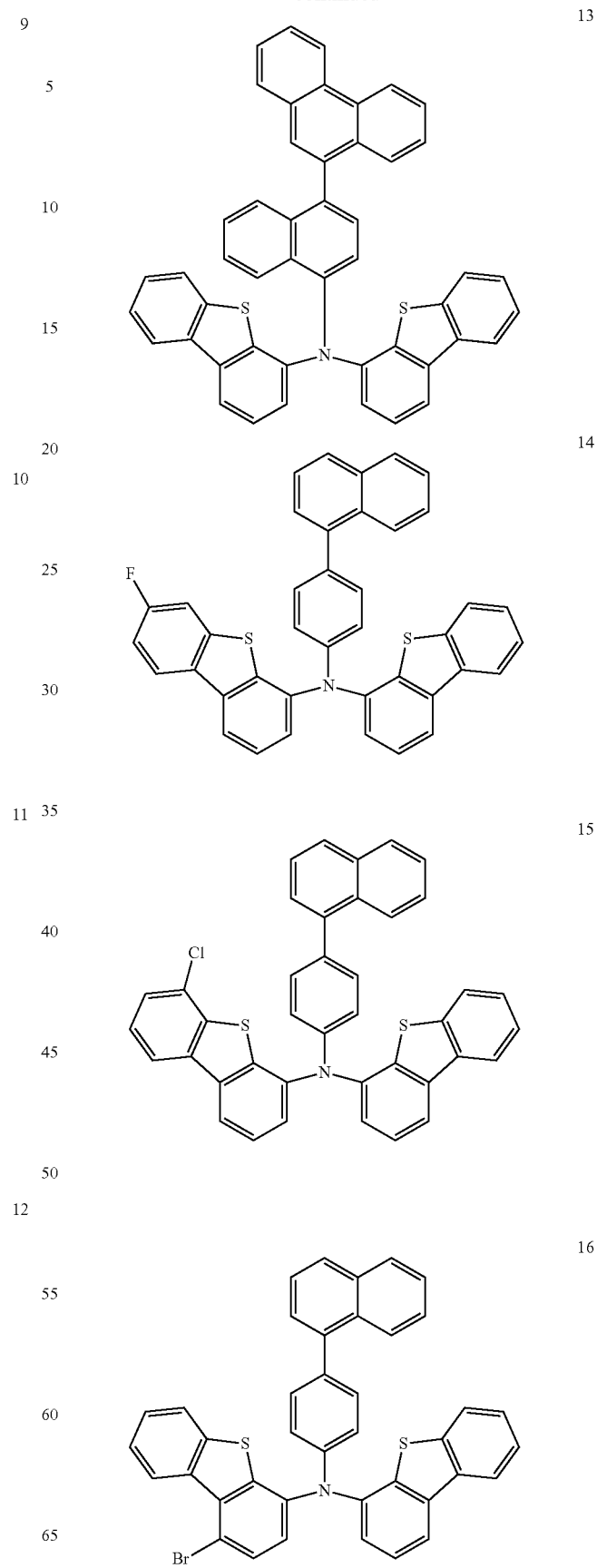

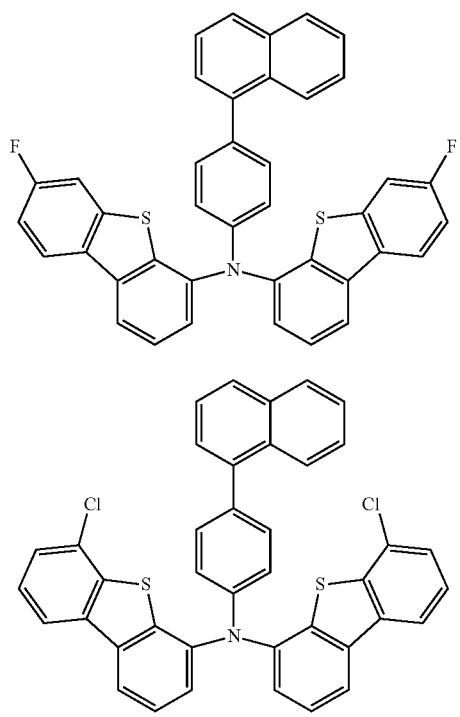
17
18
19
20
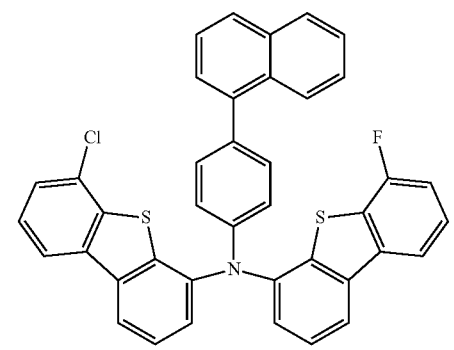
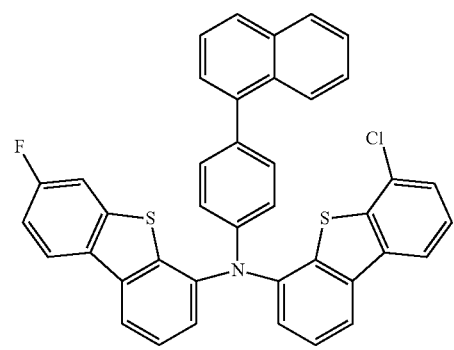
21
22
23
24
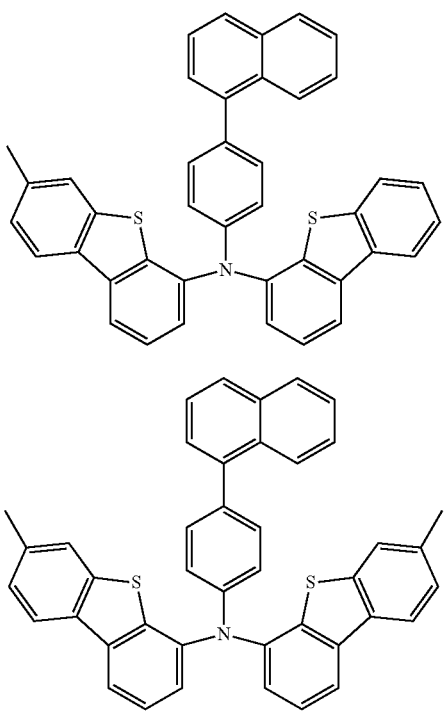
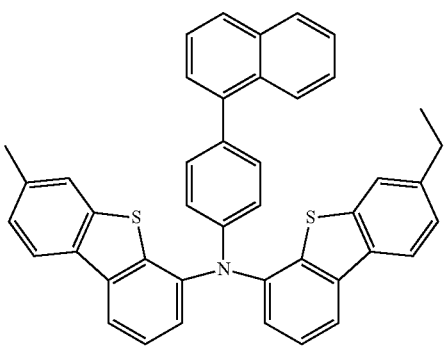
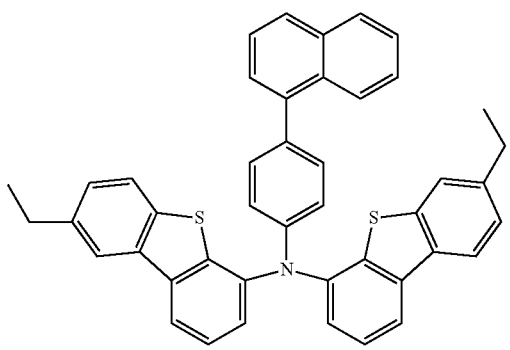

25
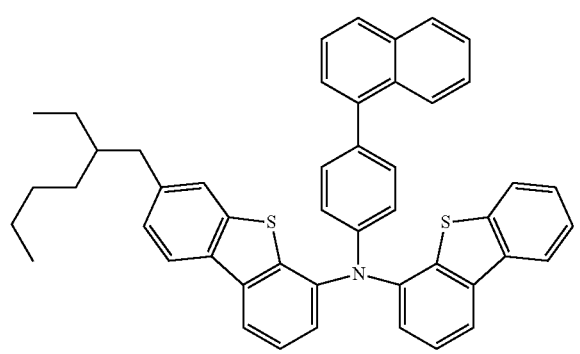
26
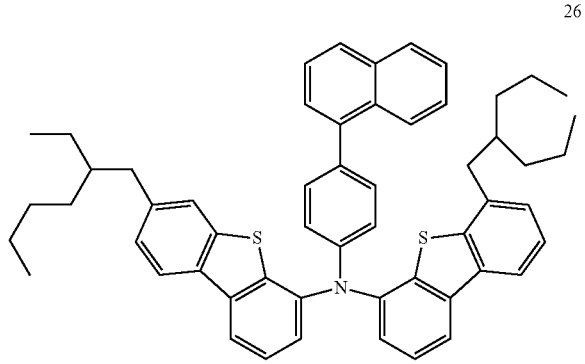
27
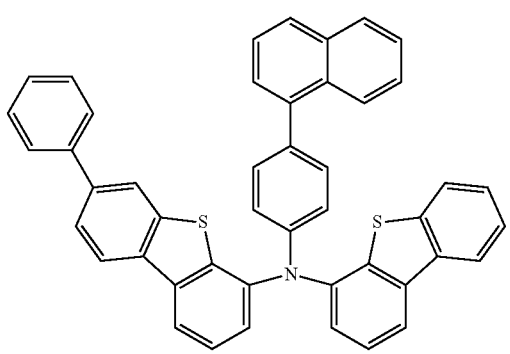
28
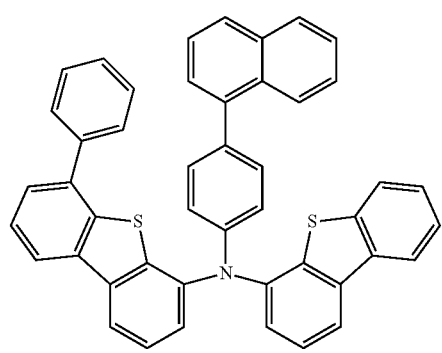
29
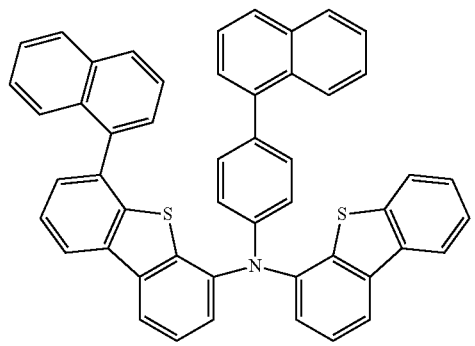
30
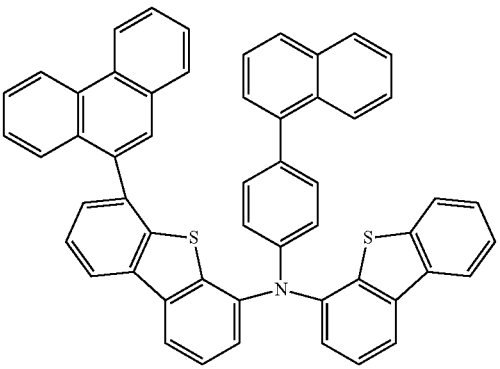
31
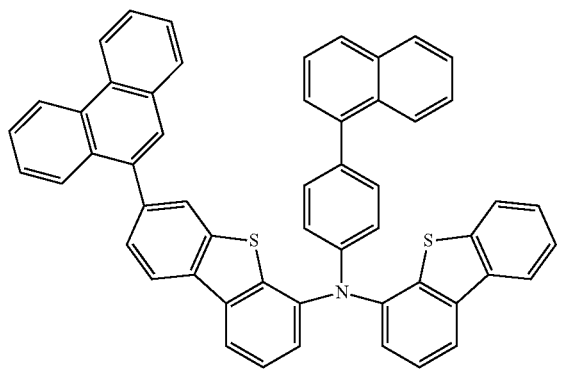
32
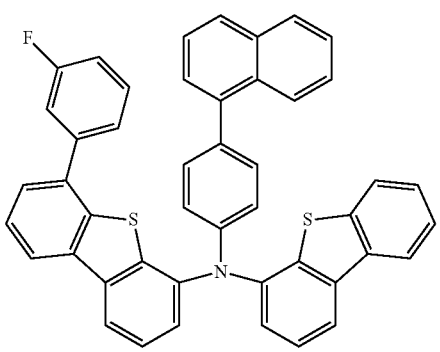

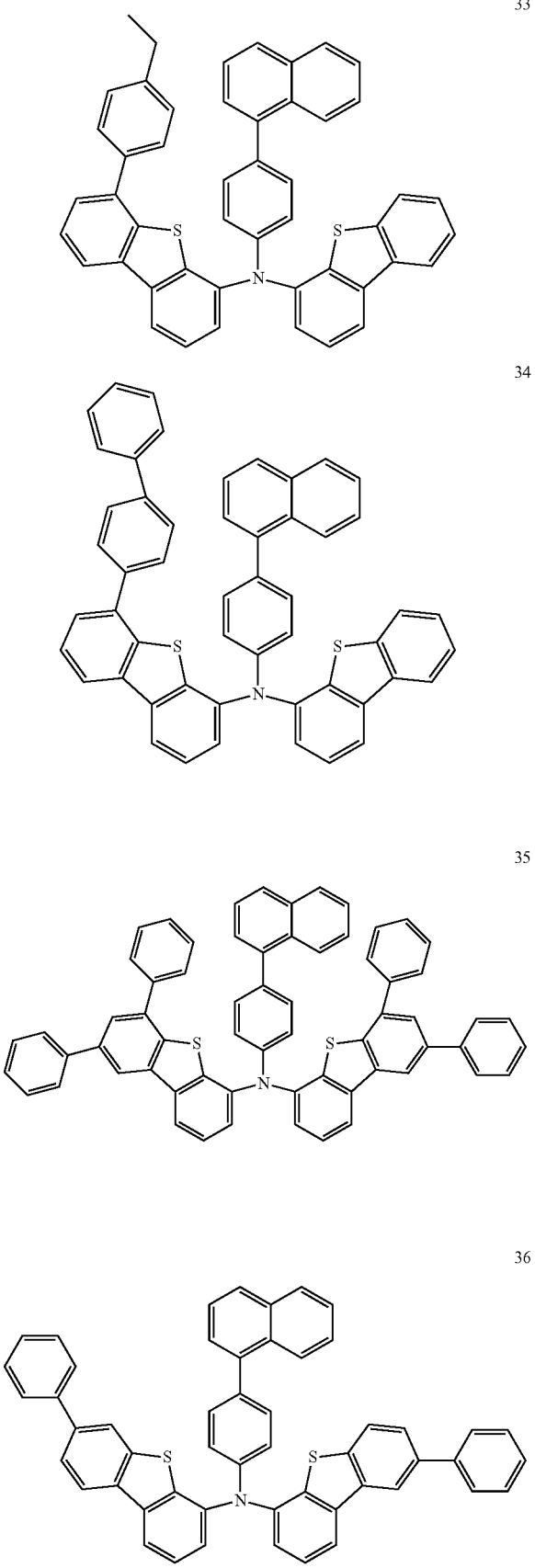
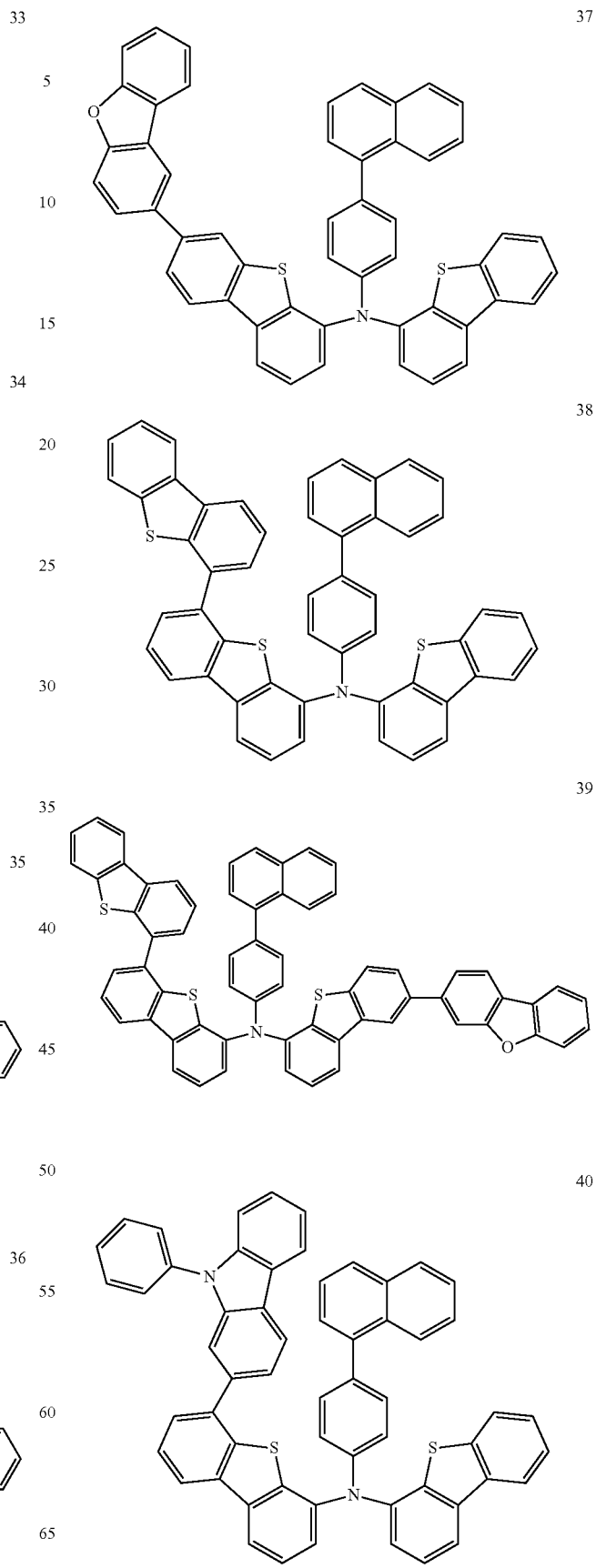

41
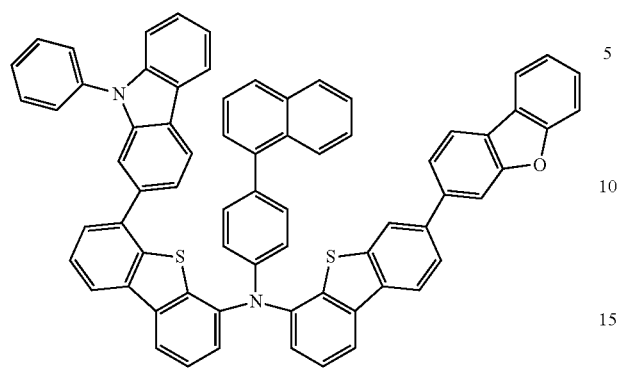
42
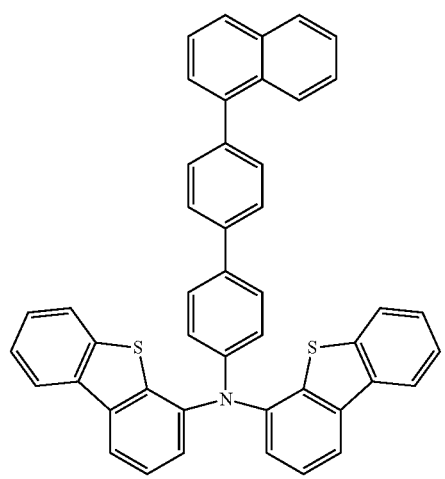
43
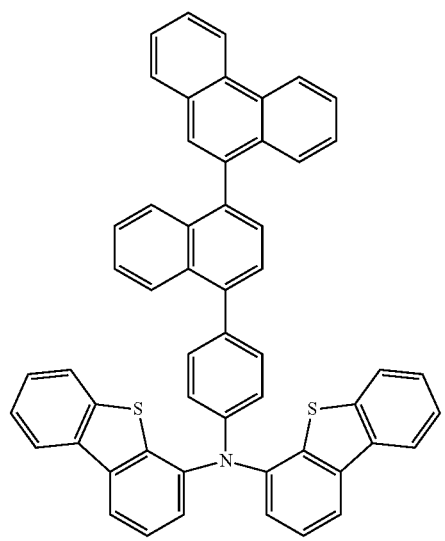
44
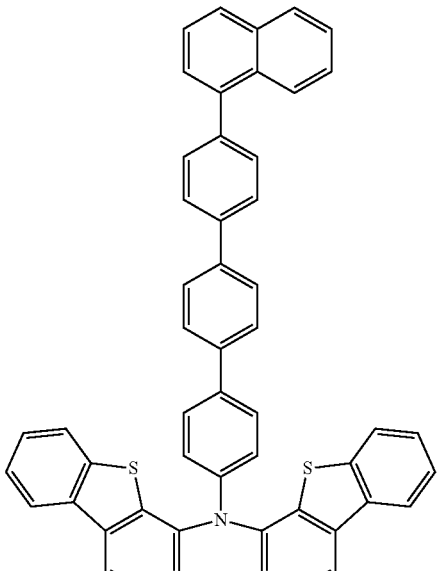
45
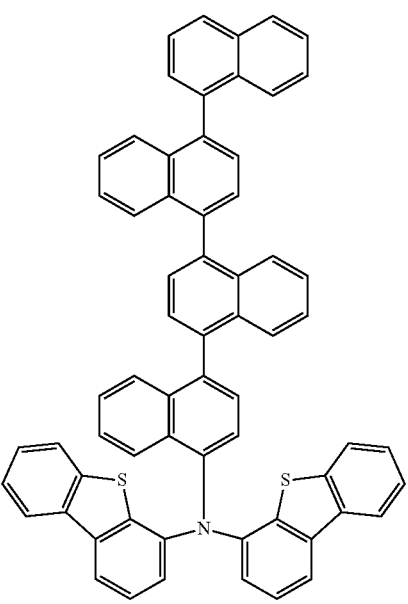

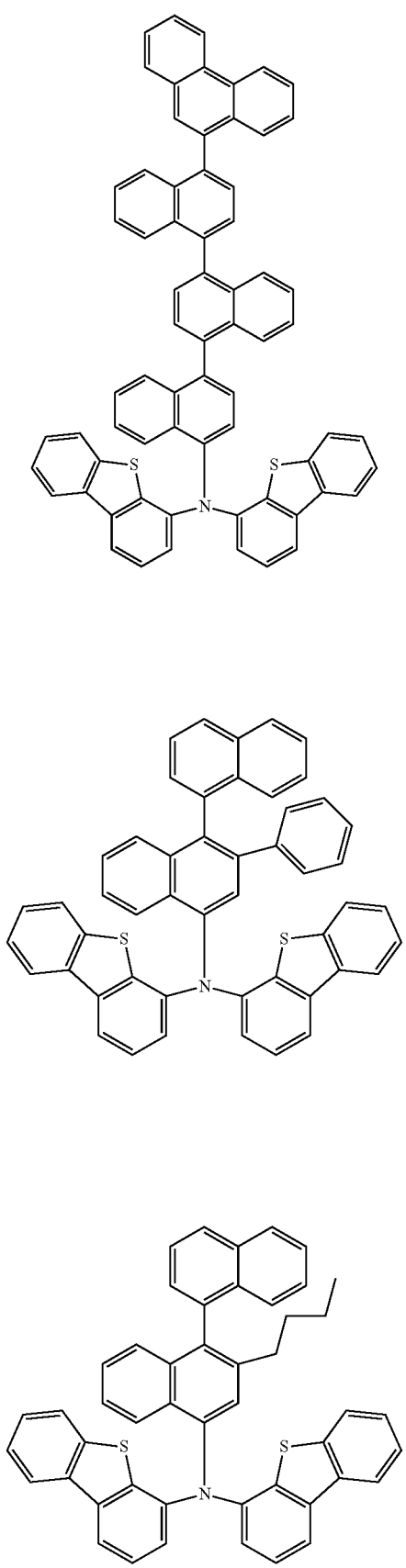
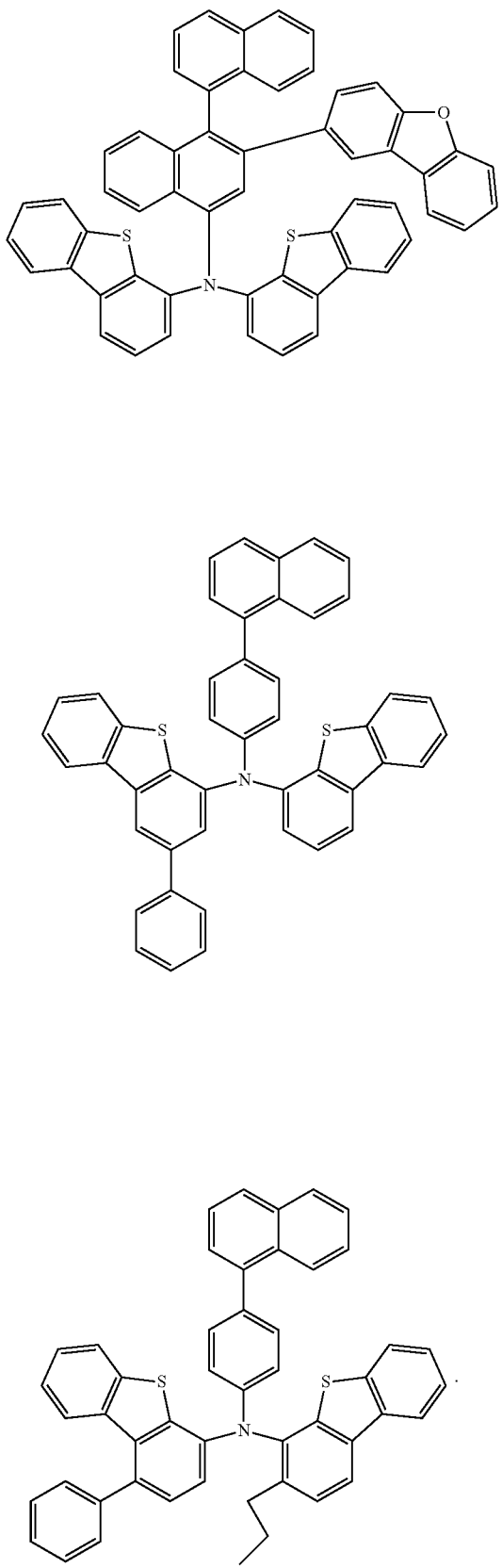

23. An amine compound represented by the following Formula 6:

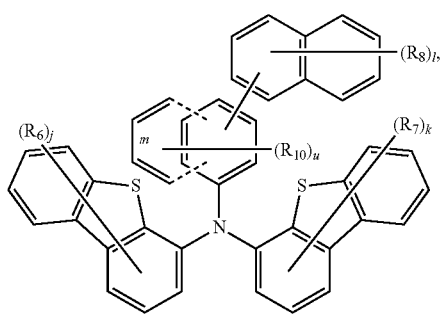

Formula 6 wherein in Formula 6,
$R_6$, $R_7$ and $R_{10}$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, each $R_8$ is independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, where a plurality of $R_8$ groups are optionally connected to form a ring, "j" and "k" are each independently an integer of 0 to 7, "l" is an integer of 0 to 7, "u" is an integer of 0 to 6, and "m" is an integer of 0 or 1.

* * * * *

UNITED STATES PATENT AND TRADEMARK OFFICE
CERTIFICATE OF CORRECTION

PATENT NO. : 11,101,442 B2  
APPLICATION NO. : 16/038981  
DATED : August 24, 2021  
INVENTOR(S) : Hideo Miyake Page 1 of 1

It is certified that error appears in the above-identified patent and that said Letters Patent is hereby corrected as shown below:

In the Claims

Column 72, Line 19, Claim 14                Delete "Lisa",  
                                            Insert -- L is a --

Column 76, Lines 15-24 approx., Claim 21    Delete " 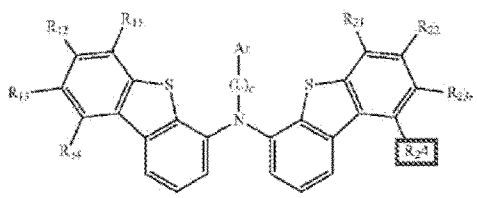 ",

Insert -- 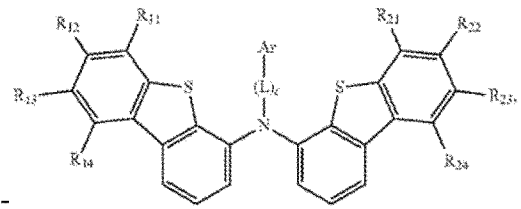 --

Column 92, Line 16, Claim 23                Delete "l",  
                                            Insert -- 1 --

Signed and Sealed this  
Twenty-fifth Day of October, 2022

Katherine Kelly Vidal  
*Director of the United States Patent and Trademark Office*